US008481676B2

United States Patent
Yamana et al.

(10) Patent No.: US 8,481,676 B2
(45) Date of Patent: Jul. 9, 2013

(54) PROTEIN AND PRODUCTION PROCESS AND USE THEREOF

(75) Inventors: Kei Yamana, Tokyo (JP); Yasunori Nakayama, Tokyo (JP); Yoshimasa Takahashi, Tokyo (JP); Eiji Ochiai, Tokyo (JP); Hitoshi Wada, Tokyo (JP); Yoshiaki Azuma, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 1013 days.

(21) Appl. No.: 12/368,219

(22) Filed: Feb. 9, 2009

(65) Prior Publication Data

US 2009/0288180 A1 Nov. 19, 2009

Related U.S. Application Data

(63) Continuation of application No. 10/575,626, filed as application No. PCT/JP2004/015620 on Oct. 21, 2004.

(30) Foreign Application Priority Data

Oct. 21, 2003 (JP) .................................. 2003-360617
May 13, 2004 (JP) .................................. 2004-143421

(51) Int. Cl.
*C07K 14/00* (2006.01)
*C07K 16/00* (2006.01)
*C07K 17/00* (2006.01)
*A61K 38/00* (2006.01)
*A61K 39/00* (2006.01)

(52) U.S. Cl.
USPC ........... 530/300; 530/402; 530/323; 530/345; 424/192.1

(58) Field of Classification Search
None
See application file for complete search history.

(56) References Cited

U.S. PATENT DOCUMENTS 6,068,990 A * 5/2000 Shintani et al. ............... 435/69.1
6,946,134 B1 * 9/2005 Rosen et al. ................. 424/192.1

FOREIGN PATENT DOCUMENTS

| CN | 1402783 A | 3/2003 |
| EP | 1219710 A1 | 3/2002 |
| WO | 00/29579 A1 | 5/2000 |
| WO | 01/23557 A1 | 4/2001 |

OTHER PUBLICATIONS

Ngo et al., 1994, The Protein Folding Problem and Tertiary Structure Prediction, pp. 492-495.*
Wells, Aditivity of Mutational Effects in Proteins, 1990, Biochemistry, vol. 26, No. 37, pp. 8509-8517.*
Rose-John et al., (1994), Biochem. J., 300, pp. 281-290.*
Y. Oshima, et al., "Expression and Localication of Tenomodulin, a Transmembrane Type Chondromodulin-I-Related Angiogenensis Inhibitor, in Mouse Eyes", Investigative Opthalmology & Visual Science, May 2003, vol. 44, No. 5, pp. 1814-1822.
K. Yamana, et al., "Molecular Cloning and Characterization of ChMIL, a Novel Membrane Molecule Similar to Chondromodulin-I", Biochemical and Biophysical Research Communication, vol. 280, No. 4, pp. 1101-1106, (2001).
Y. Hiraki, et al., "Molecular cloning of human chondromodulin-I, a cartilage-derived growth modulating factor, and its expression in Chinese hamster ovary cells", Eur. J. Biochem., vol. 260, pp. 869-878, (1999).
Y. Hiraki, et al., "Identification of Chondromodulin I as a novel endothelial cell growth inhibitor. Purification and its Localizations in the Avascular Zone of Epiphyseal Cartilage.", The Journal of Biological Chemistry, vol. 272, No. 51, pp. 32419-32426, Dec. 19, 1997.
Y. Hiraki, et al., "Inhibition of DNA synthesis and tube morphogenesis of cultured vascular endothelial cells by chondromodulin-I", FEBS Letters, vol. 415, pp. 321-324, (1997).
T. Hayami, et al., "Specific loss of chondromodulin-I gene expression in chondrosarcoma and the supression of tumor angiogenesis and growth by its recombinant protein in vivio", FEBS Letters, vol. 458, pp. 436-440, (1999).
S. Liu, et al., "Removal of Endotoxin from Recombinant Protein Preparations", Clinical Biochemistry, vol. 30, No. 6, pp. 455-463, (1997).
Hiraki, Yuji, et. al., "Chondromodulin-I as a novel cartilage-specific growth-modulating factor," Pediatr Nephrol (2001) 14:602-605.
Nakamichi, Yuko, et. al., "Chondronmodulin I is a Bone Remodeling Factor," Molecular and Cellular Biology, Jan. 2003, pp. 636-644.
Oshima, Yusuke, et. al., "Anti-angiogenic action of the C-termial domain of tenomodulin that shares homology with chondromodulin-I," Journal of Cell Science, Jan. 2004, 117, pp. 2731-2744.
Shigui Liu, et al.; Removal of Endotoxin from Recombinant Protein Preparations; Clinical Biochemistry, vol. 30, Aug. 1997, pp. 455-463.

* cited by examiner

*Primary Examiner* — Christine J Saoud
*Assistant Examiner* — Jegatheesan Seharaseyon
(74) *Attorney, Agent, or Firm* — Sughrue Mion, PLLC

(57) ABSTRACT

[Problems] To provide a polypeptide having a novel structure and showing an activity of inhibiting angiogenesis or an activity of inhibiting osteoclastogenesis, and to provide a recombinant protein by constructing a method of purifying the above protein. To provide an ingredient useful in designing remedies for tendinitis, rheumatoid arthritis, arthritis deformans, malignant tumor, etc.
[Means for Solving Problems] A novel soluble polypeptide protein.

2 Claims, 24 Drawing Sheets
(11 of 24 Drawing Sheet(s) Filed in Color)

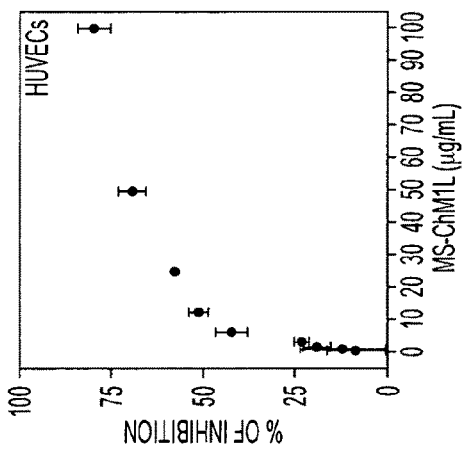
FIG. 4A
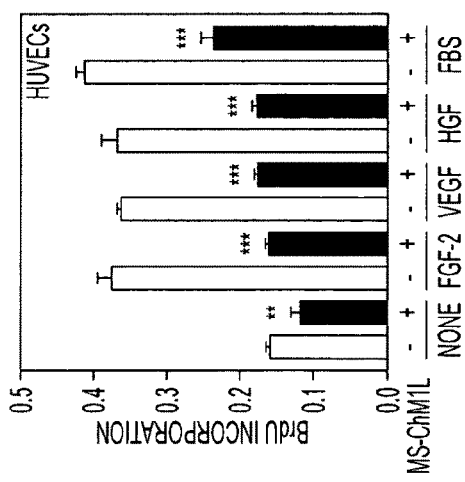
FIG. 4B
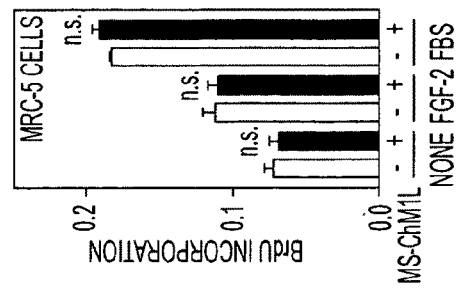
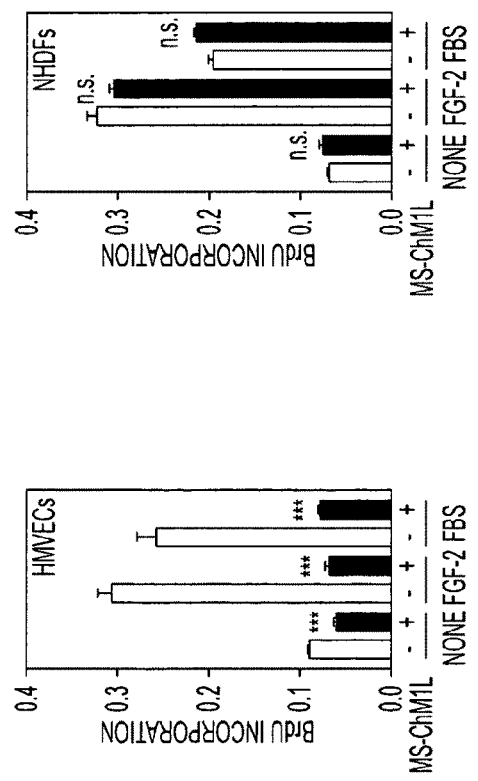
FIG. 4C
FIG. 4D
FIG. 4E

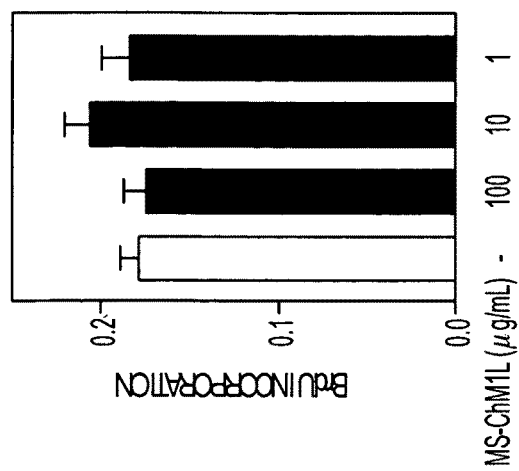
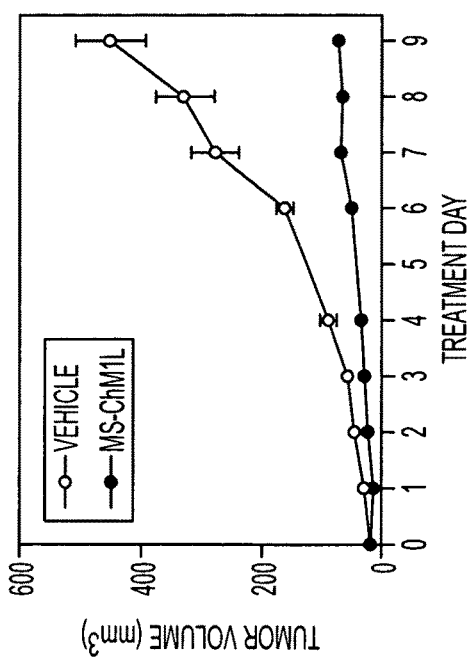
FIG. 22A
FIG. 22B

PROTEIN AND PRODUCTION PROCESS AND USE THEREOF

This application is a Continuation of application Ser. No. 10/575,626 filed Apr. 13, 2006, which is a U.S. National Stage Application of International Application No. PCT/JP2004/015620, filed Oct. 21, 2004, which claims benefit to Japanese Application Nos. 2003-360617, filed Oct. 21, 2003 and 2004-143421, filed May 13, 2004.

TECHNICAL FIELD

The present invention relates to a novel soluble protein having an activity of inhibiting angiogenesis and/or an activity of inhibiting bone resorption by osteoclast activation, a process for producing the same, and a novel diagnostic agent and therapeutic agent using the protein.

BACKGROUND ART

The "angiogenesis" refers to formation of new blood vessels in the body. For angiogenesis, there are a promoter and an inhibitor, and their balance regulates angiogenesis. It is said that the total length of the blood vascular system in an adult reaches 10 km, the surface area of vascular endothelial cells is 7000 $m^2$, and the weight thereof is 1 kg, and the blood vascular system is considered as the largest organ in human, which is distributed in every site in the living body. Angiogenesis occurs vigorously in an embryonic stage or in a process of growth, but in an adult body, angiogenesis is not observed except for special cases such as ovulation and wound healing. The blood vascular system is essential for maintaining the life, and the angiogenesis is a normal reaction in the living body.

On the other hand, abnormal angiogenesis other than that described above causes various diseases. The typical example is cancer angiogenesis. Angiogenesis in cancer tissues brings about a significant increase in cancer as well as hyper-metastasis. Accordingly, if angiogenesis through which nutrients are supplied into cancer cells were inhibited, the cancer could be kept in tumor dormancy. Folkman et al., who proposed tumor dormancy, have identified angiogenesis inhibitors produced by cancer cells and named them angiostatin and endostatin (Non-patent document 1: 0' Reilly et al., Cell, USA, Vol. 79, No. 2, pp. 315-328, Oct. 21, 1994, Non-patent document 2: 0' Reilly et al., Cell, USA, Vol 88, No. 2, pp. 277-285, Jan. 24, 1997). It was revealed that these angiogenesis inhibitors almost completely regress cancers in mice, and thereafter angiogenesis has been extensively studied. At present, many pharmaceutical companies are struggling to develop angiogenesis inhibitors and are conducting clinical tests on cancer, but do not arrive at success in overcoming cancer, angiogenesis inhibitors.

Abnormal angiogenesis also occurs in other diseases than cancer, for example diabetic retinopathy and rheumatoid arthritis, and there are a large number of reported data suggesting a possibility that such diseases can be cured by inhibiting angiogenesis. It is therefore estimated that angiogenesis inhibitors can serve as therapeutic agents not only for cancer but also for other diseases accompanied by angiogenesis.

The blood vascular system is distributed in every tissue in the body, but there are also tissues lacking in vascular network. The tissues lacking in vascular network include a cartilage, tendon, ligament and eye ball. In mesenchyme tissues, bone and muscle are rich in blood vessels and have an ability to regenerate them upon bone fracture or damage to muscle.

In the mesenchyme tissues, however, the cartilage, tendon and ligament are tissues lacking in vascular network and are hardly naturally cured upon damage or breakage. These blood-free tubular tissues are destroyed by infiltration with blood vessels, so these tissues are estimated to have an intrinsic angiogenesis inhibitor inhibiting infiltration with surrounding blood vessels.

Chondromodulin-I (ChM-I) is an angiogenesis inhibitor present in cartilage, which is purified being an about 25-kDa glycoprotein purified from fetal bovine cartilage. It is estimated to regulate infiltration of cartilage with blood vessels (Non-patent document 3).

ChM1L, being as a II-type transmembrane protein having homology with ChM-I, is found (Non-patent document 4: Yamana et al., Biochemical and Biophysical Research Communications, USA, Vol. 280. No. 4, pp. 1101-1106, Feb. 2, 2001, Patent document 1: WO 01/23557) connective tissues such as tendon and ligament and is estimated to regulate infiltration of these tissues with blood vessels (Patent document 2: WO 01/53344, Non-patent document 5: Brandau et al., Developmental Dynamics: an official publication of the American Association of Anatomists, USA, Vol. 221, No. 1, pp. 72-80, May, 2001, Non-patent document 6: Shukunami et al., Biochemical and Biophysical Research Communications, USA, Vol 280, No. 5, pp. 1323-1327, Feb. 2, 2001).

As described above, the tendon and ligament as well as the cartilage are tissues lacking in vascular network. The tendon and ligament are very important tissues connecting bones and muscles, and their damage or breakage is considered as a serious disease by which not only athletes but also ordinary people are subject to limitation in physical exercise. Thus, tendon and ligament tissues are important tissues, but as compared with cartilage, are not so investigated in fundamental and clinical studies. This is due to the absence of marker molecules expressed specifically in the tendon or ligament, in addition to difficult acquisition of tendon and ligament materials such as cells. Under these circumstances, there is demand for marker molecules capable of evaluating the degree of damage or repair in the tendon and ligament. ChM1L is expressed specifically in the tendon and ligament and is thus considered usable as a marker molecule for evaluating damage or repair in these tissues. There is also a possibility that by regulating the activity of ChM1L, damage to the tendon or ligament can be treated.

For use of ChM-I, its secretory protein and a protein such as ChM1L as angiogenesis inhibitors, however, there are many problems to be solved.

For development of a recombinant protein as a pharmaceutical preparation, its active protein should be prepared in a large amount. Generally, an expression system of using a microorganism, particularly *Escherichia coli*, is widely used in protein production in industrial scale. Expression in *Escherichia coli* is advantageous in that a very high level of recombinant protein can be obtained by using a vector capable of high-level expression as well as culture in high density.

However, *Escherichia coli* often produce an inclusion body containing the recombinant protein, which is a serious problem when *Escherichia coli* is used as a host. Actually, *Escherichia coli* produce an inclusion body therein of endostatin examined as an angiogenesis inhibitor in a clinical test, and its refolding is difficult (Non-patent document 2: 0' Reilly et al., Cell, USA, Vol 88, No. 2, pp. 277-285, Jan. 24, 1997), so a modified method is still researched at present (Patent document 3: Japanese Patent Application National Publication (Laid-Open) No. 2002-504494).

Development of ChM-I as anticancer drug by utilizing its inhibitory activity on angiogenesis has also been examined, but it is reported that *Escherichia coli* produce an inclusion body of ChM-I upon expression therein which is hardly refolded (Non-patent document 7: Yamakawa et al., The Molecular Biology Society of Japan, 25 th annual meeting, Collection of Lecture Abstracts, 2P-0206, Nov., 2001). Even if Chinese hamster ovary (CHO) cells are used as host cells, ChM-I forms an aggregation and thus requires a refolding process, which makes acquisition of a large amount of its active protein difficult (Non-patent document 8: Azizan et al., The Journal of Biological Chemistry, USA, Vol. 276, No. 26, pp. 32419-32426 Jun. 29, 2001).

It is known that *Escherichia coli* produce an inclusion body of ChM1L, as in the case of ChM-I , upon expression therein which is hardly refolded (Non-patent document 9: Hasegawa et al., The Molecular Biology Society of Japan, 25 th annual meeting, Collection of Lecture Abstracts, 2P-0770, Nov., 2001) . ChM1L can be obtained as an active protein from culture medium when it is expressed in COS7 cells. Its expression level is, however, low and an aggregation of ChM1L is observed as in the case of ChM-I, which makes acquisition of a large amount of its active protein impossible (Patent document 4: WO 00/12708) .

In some cases, protein is cleaved and secreted extracellularly. For example, it is known that tumor necrosis factor-α (TNF-α) is expressed an extracellular domain of a transmembrane as a type-II transmembrane protein and functions as a transmembrane protein, but is cleaved with a protease such as TNF-α converting enzyme and also functions as a secretory protein. It is also known that ChM-I has a type-II membrane protein structure, but undergoes processing at a protease (e.g. furin) recognition site (REHR) to secrete its C-terminal 120 amino acids extracellularly (Non-patent document 3: Hiraki et al. , The Journal of Biological Chemistry, USA, Vol. 272, No. 51, pp. 32419-32426, Dec. 19, 1997, Non-patent document 8: Azizan et al., The Journal of Biological Chemistry, USA, Vol. 276, No. 26, pp. 32419-32426 Jun. 29, 2001)

However, the secretory ChM-I consisting of the above 120 amino acid residues, even when produced by recombination, does not exhibit sufficient solubility and fails to solve the problem described above.

ChM1L has homology in amino acid sequence with ChM-I, but is free of a typical protease recognition site like what ChM-I has and is estimated to function as a transmembrane protein, and there is no report where ChM1L is found to be a secretory protein (Patent document 4: WO 00/12708, Patent document 5: WO 00/29579, Patent document 6: WO 01/23557, Patent document 7: WO 01/48203, Patent document 8: WO 01/53344, Non-patent document 4: Yamana et al., Biochemical and Biophysical Research Communications, USA, Vol. 280. No. 4, pp. 1101-1106, Feb. 2, 2001, Non-patent document 5: Brandau et al., Developmental Dynamics: an official publication of the American Association of Anatomists , USA, Vol. 221, No. 1, pp. 72-80, May, 2001, Non-patent document 6: Shukunami et al. , Biochemical and Biophysical Research Communications, USA, Vol280, No. 5, pp. 1323-1327, Feb. 2, 2001).

Patent document 1: WO 01/23557
Patent document 2: WO 01/53344
Patent document 3: Japanese Patent Application National Publication (Laid-Open) No. 2002-504494
Patent document 4: WO 00/12708
Patent document 5: WO 00/29579
Patent document 6: WO 01/23557
Patent document 7: WO 01/48203
Patent document 8: WO 01/53344

Non-patent document 1: O' Reilly et al., Cell, USA, Vol. 79, No. 2, pp. 315-328, Oct. 21, 1994
Non-patent document 2: O' Reilly et al., Cell, USA, Vol. 88, No. 2, pp. 277-285, Jan. 24, 1997
Non-patent document 3: Hiraki et al., The Journal of Biological Chemistry, USA, Vol. 272, No. 51, pp. 32419-32426, Dec. 19, 1997
Non-patent document 4: Yamana et al., Biochemical and Biophysical Research Communications, USA, Vol. 280. No. 4, pp. 1101-1106, Feb. 2, 2001
Non-patent document 5: Brandau et al., Developmental Dynamics: an official publication of the American Association of Anatomists, USA, Vol. 221, No. 1, pp. 72-80, May, 2001
Non-patent document 6: Shukunami et al., Biochemical and Biophysical Research Communications, USA, Vol. 280, No. 5, pp. 1323-1327, Feb. 2, 2001
Non-patent document 7: Yamakawa et al., The Molecular Biology Society of Japan, 25$^{th}$ annual meeting, Collection of Lecture Abstracts, 2P-0206, November, 2001
Non-patent document 8: Azizan et al., The Journal of Biological Chemistry, USA, Vol. 276, No. 26, pp. 32419-32426, Jun. 29, 2001
Non-patent document 9: Hasegawa et al., The Molecular Biology Society of Japan, 25$^{th}$ annual meeting, Collection of Lecture Abstracts, 2P-0770, November, 2001

DISCLOSURE OF INVENTION

As described above, application of wild-type ChM-I and ChM1L to pharmaceutical preparations etc. is disadvantageous in respect of their large-scale production, and thus there is need for development of other substances or at least development of a method of preparing wild-type ChM-I or ChM1L easily.

The present inventors extensively studied wild-type transmembrane ChM1L, and as a result they found a new soluble polypeptide (S-ChM1L) having an activity of inhibiting angiogenesis which can be a secretory protein of ChM1L which has not reported so far, and further confirmed that S-ChM1L and its modified polypeptide (MS-ChM1L) have an activity of inhibiting the bone resorption caused by osteoclasts in addition to the activity of inhibiting angiogenesis.

That is, the present invention relates to (1) a polypeptide comprising an amino acid sequence represented by SEQ ID NO: 9, or a polypeptide comprising an amino acid sequence having at least 70% homology with an amino acid sequence represented by SEQ ID NO: 9 and having an activity of inhibiting angiogenesis and/or an activity of inhibiting bone resorption. The invention also relates to (2) the polypeptide according to the above-mentioned (1), which further has amino acid residues added to the N-terminal and/or C-terminal thereof, (3) the polypeptide according to the above-mentioned (2), wherein the amino acid residues added to the N-terminal thereof consist of an amino acid sequence beginning at methionine; (4) the polypeptide according to the above-mentioned (2) or (3), wherein the amino acid residues added to the N-terminal and/or C-terminal thereof consist of an amino acid sequence containing a tag sequence consisting of 6 to 8 consecutive histidine residues and/or a FLAG tag sequence; (5) the polypeptide according to the above-mentioned (2) or (3), wherein the amino acid residues added to the N-terminal and/or C-terminal thereof consist of an amino acid sequence of an *Aequorea victoria*-derived fluorescence protein or its analogue or a secretory alkali phosphatase or its analogue; (6) the polypeptide according to the above-mentioned (1), wherein the amino acid residues added to the N-terminal and/or C-terminal thereof contain modified amino acid residues; (7) the polypeptide according to the above-mentioned (6), wherein the amino acid residues added to the N-terminal thereof are glutamine or pyroglutamine residues; and (8) the polypeptide according to the above-mentioned (6), wherein the modified amino acid residues have at least one modified group selected from the group consisting of an acetyl group, formyl group, biotin group, Boc group and Fmoc group.

The present invention also relates to (9) a nucleic acid molecule having a nucleotide sequence encoding an amino acid sequence represented by SEQ ID NO: 9; (10) a nucleic acid molecule having a nucleotide sequence from positions 4 to 243 of SEQ ID NO: 3, or a nucleic acid molecule which hybridizes under stringent conditions to a complementary sequence to the sequence from positions 4 to 243 in SEQ ID NO: 3 and having a nucleotide sequence encoding a polypeptide having an activity of inhibiting angiogenesis and/or an activity of inhibiting bone resorption; (11) a nucleic acid molecule having a nucleotide sequence encoding the polypeptide according to any one of the above-mentioned (2) to (6); (12) a vector containing the nucleic acid molecule according to any one of the above-mentioned (9) to (11); and (13) a host cell transformed with the vector of the above-mentioned (12).

The present inventors have also found that the above polypeptide can be prepared as a soluble polypeptide by using a suitable recombinant host cell, and such soluble protein can be easily purified from contaminants such as endotoxin derived from the host cell in the presence of a denaturant and a specific surfactant at the time of preparation.

That is, the present invention also relates to (14) a process for producing the polypeptide according to any one of the above-mentioned (1) to (8), which comprises culturing the transformed host cell of the above-mentioned (13) and recovering the expressed polypeptide; (15) the process for producing a polypeptide according to the above-mentioned (14), which comprises recovering, in the presence of a protein denaturant, a polypeptide-containing extract from the transformed host cell; (16) the process for producing a peptide according to the above-mentioned (14) or (15), which comprises treating the extract recovered from the host cell with TRITON™ X-114 (polyethylene monoctylphenyl ether)followed by centrifuging it to remove a pyrogen; (17) the process for producing a polypeptide according to any one of the above-mentioned (14) to (16), wherein the pH of the polypeptide-containing solution is adjusted in the range of pH 8.0 to 8.5 in all steps after recovery of the polypeptide-containing extract from the host cell; (18) a process for producing recombinant human ChM-I or recombinant human ChM1L by using a recombinant host cell capable of exhibiting human ChM-I or human ChM1L, which comprises recovering an extract containing human recombinant ChM-I or human recombinant ChM1L from the recombinant host cell in the presence of a protein denaturant, treating the extract with Triton X-114 and centrifuging it to remove a pyrogen; and (19) the process according to the above-mentioned (18), wherein the pH of the polypeptide-containing solution is adjusted in the range of pH 8.0 to 8.5 in all steps after recovery of the extract.

Further, the present invention provides a pharmaceutical composition comprising the polypeptide according to any one of the above-mentioned (1) to (8), particularly (21) the pharmaceutical composition according to claim 20, which is an angiogenesis inhibitor and/or an inhibitor of osteoclast activation, as well as a diagnostic composition used in any morbid state associated with angiogenesis or bone resorption, such as tendinitis, rheumatoid arthritis, arthritis deformans, malignant tumor, diabetic retinopathy, glaucoma, psoriasis, keloid and arteriosclerosis.

Furthermore, the present invention provides a transgenic non-human animal manipulated genetically so as to contain the nucleic acid molecule according to any one of the above-mentioned (9) to (11).

EFFECT OF THE INVENTION

As described later, the soluble protein of the present invention has an activity of inhibiting the bone resorption caused by activation of osteoclasts in addition to an activity of inhibiting angiogenesis and a dramatic therapeutic effect can be expected when the protein is used as a pharmaceutical preparation to inhibit angiogenesis and activation of osteoclasts particularly on rheumatoid arthritis and bone metastasis tumor.

The soluble protein of the present invention is a protein consisting of a partial sequence of naturally occurring ChM1L and thus exhibits low antigenicity, and can be prepared in a large amount without a refolding step in production by using recombinant cells.

Further, the removal of host cell-derived endotoxin to such a level as to permit the soluble protein to be administered into the living body, which is necessary for production using recombinant cells, can be easily effected in the process for producing the soluble protein according to the present invention. This process is also effective for purification of wild-type ChM1L, which has been difficult in conventional recombination production.

BEST MODE FOR CARRYING OUT THE INVENTION

<Soluble Polypeptides S-ChM1L and MS-ChM1L or Nucleic Acid Molecules Encoding Them>

The present invention relates to a novel soluble polypeptide having an activity of inhibiting angiogenesis and/or an activity of inhibiting bone resorption by osteoclasts.

The phenomenon "angiogenesis" wherein capillary blood vessels are newly formed is known to occur through the following steps: (1) digestion with matrix metalloprotease (MMP) etc. in an extracellular matrix in a blood vessel basement membrane and therearound, (2) migration of vascular endothelial cells, (3) growth of the vascular endothelial cells, and (4) capillary tube formation. The inhibition of angiogenesis referred to in the present invention means an activity of substantially inhibiting angiogenesis by participation in any of the above steps.

As will be described later in the Examples, a polypeptide having an amino acid sequence represented by SEQ ID NO: 9 has an activity of inhibiting all the steps (1) to (4). Accordingly, the polypeptide of the present invention can be considered usable as a therapeutic agent for diseases accompanied by angiogenesis, such as cancer, rheumatoid arthritis, psoriasis and diabetic retinopathy.

Surprisingly, it is found that the soluble polypeptide of the present invention also has a function of inhibiting bone resorption by osteoclasts. The inhibition of bone resorption in the present invention refers to an activity of inhibiting the bone resorption caused by activation of osteoclasts.

Generally, bone metabolism is regulated by balance between bone formation and resorption by osteoclasts. Osteoporosis, rheumatoid arthritis, bone Paget's disease, hypercalcemia, alveolar bone loss, renal osteodystrophy, osteolytic tumor, and bone metastatic tumor are known to be the diseases caused by abnormality of bone methabolism. Accordingly, the soluble polypeptide of the present invention can also be used as a therapeutic agent for the diseases associated with bone resorption by osteoclasts. Particularly, rheumatoid arthritis is a disease wherein bone/cartilage destruction by osteoclasts as well as inflammation and growth of synovial cells accompanied by angiogenesis is problematic. Especially, bone metastatic tumor is a disease in which angiogenesis is closely involved in growth and metastasis of the tumor and osteoclasts are closely involved in bone lysis by bone resorption, and thus the soluble polypeptide of the present invention is extremely advantageous over existing chemicals.

The soluble polypeptide of the present invention is typically a polypeptide (S-ChM1L) having an amino acid sequence represented by SEQ ID NO: 9, and may be a polypeptide (MS-ChM1L) having one or more additional amino acid residues, particularly amino acid residues constituting a peptide other than ChM1L, at both the ends of the polypeptide (S-ChM1L). For example, a polypeptide having glutamine or pyroglutamine residues added to the N-terminal of the amino acid sequence represented by SEQ ID NO: 9 also has an activity of inhibiting angiogenesis and an activity of inhibiting bone resorption. The polypeptide having a suitable tag sequence, typically a histidine tag or a FLAG tag added to the N-terminal of the amino acid sequence represented by SEQ ID NO: 9 still has an activity of inhibiting angiogenesis and an activity of inhibiting bone resorption. The polypeptide having an amino acid sequence of *Aequorea victoria*-derived fluorescence protein or secretory alkali phosphatase added in place of the tag sequence still maintains the desired functions.

Accordingly, the polypeptide (S-ChM1L) having the amino acid sequence represented by SEQ ID NO: 9 and the polypeptide (MS-ChM1L) having amino acids of a different protein added to both the ends of the polypeptide (S-ChM1L) should be understood to fall within the scope of the present invention.

A polypeptide comprising partial amino acids deletion or substitution in the amino acid sequence represented by SEQ ID NO: 9 also falls within the scope of the present invention and is construed as MS-ChM1L insofar as it is a polypeptide having an activity of inhibiting angiogenesis and/or an activity of inhibiting bone resorption.

For example, a soluble polypeptide having the amino acid sequence of S-ChM1L wherein one or more amino acid residues are substituted by other chemically or structurally similar amino acids can be obtained. Specific example of substitution between such chemically or structurally similar amino acids, that is, highly conserved substitution of amino acids, are well known to those skilled in the art and can be exemplified by, for example, substitution between glycine (Gly) and proline (Pro), Gly and alanine (Ala) or valine (Val), leucine (Leu) and isoleucine (Ile), glutamic acid (Glu) and glutamine (Gln), aspartic acid (Asp) and asparagine (Asn), cysteine (Cys) and threonine (Thr), Thr and serine (Ser) or Ala, lysine (Lys) and arginine (Arg).

Accordingly, even a soluble polypeptide consisting of an amino acid sequence which is different from the amino acid sequence represented by SEQ ID NO: 9 such a soluble polypeptide is an embodiment of MS-ChM1L insofar as the difference is the highly conserved amino acid substitution as described above and simultaneously the polypeptide has an activity of inhibiting angiogenesis and/or an activity of inhibiting bone resorption.

The amino acid sequence of the above mentioned MS-ChM1L has 70% or more, preferably 80% or more, more preferably 90% or more homology with the amino acid sequence set forth in SEQ ID NO: 9.

The soluble polypeptide of the present invention can be easily prepared by chemical synthesis or general genetic recombination techniques.

Preparation by genetic engineering techniques includes a method that comprises expressing a DNA consisting of a nucleotide sequence encoding an amino acid sequence of the soluble polypeptide of the present invention, in a suitable host cell, and then recovering the polypeptide. For example, typically a DNA consisting of a nucleotide sequence encoding an amino acid sequence wherein an amino acid sequence beginning at methionine is added to the N-terminal of the amino acid sequence set forth in SEQ ID NO: 9 is prepared, then integrated into a suitable vector and used to transform a host cell, followed by expressing the polypeptide.

For the purpose of the improvement of stability, solubility, efficient purification, the efficiency of expression of the polypeptide and detection of a produced molecule, a DNA consisting of a nucleotide sequence encoding the amino acid sequence set forth in SEQ ID NO: 9 to which an amino acid sequence of an arbitrary peptide was added may be prepared, then integrated into a suitable vector and used to transform a host cell, followed by expressing the polypeptide.

For example, the soluble polypeptide of the present invention can be formed in such a form as to contain a His or FLAG tag sequence having 6 or more consecutive histidine residues by using a nucleotide sequence encoding such tag sequence. The soluble polypeptide having such constitution is advantageous in that it can be easily purified by a metal chelate carrier or an antibody.

As another example, the soluble polypeptide of the present invention can be expressed in the form of a fusion protein, that is, the protein to which an amino acid sequence constituting an *Aequorea victoria*-derived fluorescence protein or a secretory alkali phosphatase was added. The fusion protein with the *Aequorea victoria*-derived fluorescence protein can be easily detected by measuring its fluorescence intensity, and the fusion protein with the secretary alkali phosphatase can be easily detected by measuring the intensity of coloration, emission or fluorescence generated upon reaction of the enzyme with its substrate.

In this case, the fusion protein as the soluble polypeptide of the present invention can be obtained typically by binding a nucleotide sequence encoding the *Aequorea victoria*-derived fluorescent protein or the secretory alkali phosphatase to the 5'- or 3'-terminal of a gene sequence encoding the polypeptide (S-ChM1L) consisting of the amino acid sequence set forth in SEQ ID NO: 9 in such a form as to enable translation of the amino acid sequence of each protein, followed by integrating the product into an expression vector and expressing it in a suitable host.

The soluble protein of the present invention expressed in a form fused protein with an arbitrary amino acid sequence can be obtained in such a form that the polypeptide corresponding to S-Ch1ML and its added sequence are bound to each other, or in such a form that its added amino acid sequence is removed. In an example of a method of removing the added amino acid sequence, the gene is constructed in such a way that the sequence containing the soluble polypeptide is bound to the added sequence via Lys residue and is then expressed to afford a protein which is then cleaved at the C-terminal side of lysine residue by treatment with endopeptidase Lys-C (EC3.4.21.50) followed by purification thereof, whereby the polypeptide containing the soluble polypeptide sequence can be recovered.

Any procedures described above can be carried out by various methods generally utilized by those skilled in the art or by utilizing known methods such as a method of enzymatically or chemically associating a polypeptide (Hermanson et al.) or Bioconjugate Techniques (USA, 1996, Academic Press).

The soluble polypeptide of the present invention can be prepared by modification of a soluble polypeptide derived from living tissues or produced by genetic engineering techniques. It is known that proteins, peptide hormones, etc. in the living body occur sometimes in such a form that their N-terminal has been converted into pyroglutamic acid or modified with an acetyl group, formyl group etc. by which the stability of the proteins or peptide hormones is improved and their activity is changed. Accordingly, the soluble polypeptide of the present invention can be used if necessary in such a form that the N-terminal of its molecule is modified after translation. In one example of a method of obtaining such molecule, the sequence containing the soluble polypeptide molecule is expressed such that the N-terminal is a glutamic acid residue, and the resulting polypeptide is treated under acidic conditions such as those in 5 to 10% acetic acid solution or the like, whereby the molecule whose N-terminal residue is converted into pyroglutamic acid can be obtained (Park et al., Proceedings of the National Academy of Sciences of the United States of America (USA), pp. 22046-2050, March, 1991). In another example, a polypeptide containing the soluble polypeptide sequence of the present invention expressed such that N-terminal becomes an arbitrary amino acid residue having an α-amino group is treated with sulfo-NHS-acetate or acetic anhydride, whereby the peptide having an acetylated N-terminal can be obtained. In addition, the obtained polypeptide containing the soluble polypeptide sequence can be modified by treatment with a compound such as a fluorescent substance.

The ChM1L modified by amino acid substitution or the molecule having homology with ChM1L, obtained by the methods described above, can be prepared by the same method as a method of preparing a recombinant protein described later and can be confirmed to have an activity of inhibiting angiogenesis and an activity of inhibiting bone resorption by methods described in Examples 5 to 13.

<Recombinant Protein>

Expression and purification of the soluble polypeptide of the present invention are carried out typically by preparing a recombinant DNA capable of expressing a gene encoding the polypeptide, transforming a host cell by the recombinant DNA into a host cell, and culturing the resulting transformant. The host cell may be either an eucaryotic host cell or a procaryotic host cell.

The eucaryotic host cell includes vertebrate cells, yeasts, and insect cells. The vertebrate cells include, for example, CHO cells, 293T cells and COS7 cells.

As an expression vectors used for vertebrates, an expression vector harboring a promoter located upstream from a gene to be expressed and a polyadenylation site and a transcription termination sequence downstream from the gene can be usually used. Examples of the expression vector include for example pSV2dhfr (Mol. Cell. Biol., 854, 1981), PCDNA3.1(+)™ (Invitrogen) (expression vector) and pCAGGS (Gene, 108, 193-200, 1991), which have an SV40 early promoter.

As a means of expressing an objective protein in eucaryotic cells, many systems are known per se in the art. For example, "Expression of Protein in Yeasts" described in JP-A 57-159489 is mentioned as a system of expression in yeasts, "Process for Producing Recombinant Baculovirus Expression Vector" in JP-A 60-37988 is mentioned as a system of expression in insect cells, and "Improvement of Eucaryotic Expression" in JP-A 2-171198 is mentioned as a system of expression in mammalian cells, and as a matter of course, there are many systems other than those mentioned above.

A gene encoding the soluble polypeptide of the present invention can be expressed in procaryotic host cells such as *Escherichia coli, Bacillus subtilis* and *Streptomyces. Escherichia coli* frequently used as the host cell includes, but is not limited to, *Escherichia coli* K12 or the like, and the vector frequently used includes, but is not limited to, pBR322 and modified vectors thereof, and a wide variety of known bacterial strains and vectors can be used. Examples of the promoter include, but are not limited to, promoters for *Escherichia coli* lactose (lac), *Escherichia coli* trp etc. Any promoters described above have been previously characterized, are well known to those skilled in the art and can be constructed by synthesis or from known plasmids.

A nucleotide sequence of a gene encoding the soluble polypeptide of the present invention or a recombinant plasmid or recombinant virus containing the same can be modified or altered in various ways. For example, the whole coding region of the polypeptide can, because of degeneracy of genetic code, be subjected to nucleotide substitution without changing its encoded amino acids. Such sequence can be deduced from the amino acid sequence of the protein and can be constructed by the following conventional synthesis methods. Such synthesis can be carried out substantially according to a method of Itakura et al. (Science, 198, 1059, 1977) and a method of Crea et al. (Proc. Natl. Acad. Sci. USA, 75, 5765, 1978). Accordingly, the present invention is not limited to the particularly illustrated nucleotide sequences, plasmids and viruses.

As the method of introducing the thus obtained desired gene into a host cell and the method of transformation therewith, a wide variety of general methods can be used. The resulting transformant can be cultured in a usual manner to produce the soluble polypeptide of the present invention. Depending on the host cell used, the medium used in culturing the same can be suitably selected from a wide variety of customarily used mediums, and the culture is carried out under conditions suitable for growth of the host cell.

By the methods described above, the protein is produced intracellularly, extracellularly or on a cell membrane in the transformant. The soluble polypeptide of the present invention can be separated and purified as desired by various separation procedures utilizing its physical properties, chemical properties etc. (see Biochemical Data Book II, first edition, first print, pp. 1175-1259, edited by the Japanese Biochemical Society, Jun. 23, 1980 by Tokyo Kagaku Dojin Co., Ltd.; Arakawa et al., Biochemistry, USA, Vol. 25, No. 25, pp. 8274-8277 (1986), Dec. 16, 1986; Langley et al., European Journal of Biochemistry, Germany, Vol. 163, No. 2, pp. 313-321, May 2, 1987). The method can be exemplified by, for example, usual re-constitution treatment, treatment with a protein precipitation agent (salting-out), centrifugation, osmotic shock procedure, disruption by sonication, ultrafiltration, gel filtration, various kinds of liquid chromatography such as absorption chromatography, ion exchange chromatography, affinity chromatography and high performance liquid chromatography (HPLC), dialysis, and combinations thereof. When a protein having an affinity tag fused with the protein is expressed, this tag can be used in affinity purification. As referred to herein, the affinity tag includes, for example, a polyhistidine tag (His tag, Sisk et al., Journal of Virology, USA, Vol. 68, No. 2, pp. 766-775, February 1994) and a FLAG tag (Hopp et al., Biotechnology, Vol. 6, pp. 1204-1210, 1988). Expression and detection of the soluble polypeptide (MS-ChM1L) fused with these affinity tags can be carried out as described in Example 1, and purification of MS-ChM1L with these tags can also be carried out as described in Example 3. The process for producing the soluble polypeptide of the present invention will be described specifically in more detail in Example 3.

<Synthesis Peptide>

The method of preparing the soluble polypeptide of the present invention includes methods of chemically synthesizing the polypeptide.

In this case, generally used peptide synthesis methods such as solid phase synthesis method and liquid phase synthesis method can be used. With respect to condensation in peptide synthesis, protection of amino acid residues and elimination of protective groups after synthesis, known methods can be used (Izumiya et al., Peptide Gosei-no-Kiso to Jikken (Basics and experiments of peptide synthesis), published by Maruzen Co. (1975); Yajima et al., Seikagaku Jikken Koza (Biochemical Experiment) 1, Tanpakushitsu no Kagaku (Chemistry of Proteins) IV, edited by the Japanese Biochemical Society and published in 1977 by Tokyo Kagaku Dojin Co., Ltd.). The whole peptide sequence of the soluble polypeptide protein can be synthesized all at once, or partial peptides of the protein can be synthesized respectively and then condensed with one another to form the soluble polypeptide (Shin-Seikagaku Jikken Koza (New Biochemical Experiment), Tanpakushitsu (Protein) IV, Gosei Oyobi Hatsugen (Synthesis and Expression) edited by the Japanese Biochemical Society, 1991 by Tokyo Kagaku Dojin Co., Ltd.). An α-amine of amino acid used in peptide synthesis is usually protected with tBoc group or Fmoc group, and the peptide can be finally obtained in a form having these protective groups remaining thereon or in a deprotected form. If necessary, the deprotected amino terminal of the peptide can be modified enzymatically or chemically with pyroglutamic acid, an acetyl group or formyl group (Hermanson et al., Bioconjugate Techniques (USA), Academic Press, 1996). In a specific example, a peptide containing the sequence of the soluble polypeptide is synthesized in a form having glutamine at the N-terminal thereof, and then the peptide can be cyclized by treatment with dilute acid such as 5 to 10% acetic acid solution to convert the N-terminal glutamine into pyroglutamic acid (Park et al., Proceedings of the National Academy of Sciences of the United States of America (USA), pp. 22046-2050, March, 1991).

<Antibody>

An antibody to the soluble polypeptide of the present invention can be used in diagnosis and treatment of bone and joint diseases. For example, a method of using the antibody, such as Western blotting, immunoprecipitation or ELISA can be used in diagnosis.

The antibody used above can be obtained by techniques known to those skilled in the art. The antibody used in the present invention can be a polyclonal or monoclonal antibody (Milstein et al., Nature, England, Vol. 305, No. 5934, pp. 537-540, Oct. 6, 1983). For example, the polyclonal antibody to the soluble polypeptide of the present invention can be recovered from serum etc. of a mammal sensitized with the polypeptide as antigen. The monoclonal antibody to the polypeptide can be recovered from a culture of a cloned hybridoma obtained by isolating an immune cell from a mammal sensitized with the antigen and then fusing the cell with a myeloma cell or the like.

For detection of the soluble polypeptide of the present invention or ChM1L protein, these antibodies may be suitably labeled. Without labeling the antibody, the soluble polypeptide of the present invention or ChM1L protein can also be detected indirectly by labeling a substance (for example, protein A or protein G) binding specifically to the antibody. The specific detection method includes, for example, the ELISA method.

The soluble polypeptide of the present invention or its partial peptide used as the antigen can be obtained for example by integrating a gene encoding the peptide, or a part thereof, into an expression vector, introducing it into a suitable host cell to create a transformant, culturing the transformant to express a recombinant protein, and purifying the expressed recombinant protein from the cultured transformant or its culture supernatant. Alternatively, an oligopeptide consisting of the amino acid sequence encoded by the gene or its partial amino acid sequence can be chemically synthesized and used as immune antigen. A mouse, rat, rabbit, goat, horse, hamster etc. are used for immunization.

<Diagnostic Method>

In the diagnostic method of the present invention, a biological sample collected from an examinee is usually used as a sample. The biological sample is preferably a blood sample. Whole blood, or plasma or serum obtained from whole blood, can be used as the blood sample. As the biological sample in the present invention, it is possible to use not only blood but also synovial fluid, a joint cartilage fragment collected by biopsy, synovial tissues, tendon tissues, ligament tissues, muscle tissues, and tear fluid. Methods of collecting these biological samples are known.

When a lysate is prepared from the biological sample, the lysate can be used as a sample for immunological measurement of the soluble polypeptide of the present invention or ChM1L. For extracting the lysate of the biological sample, a commercial kit can be conveniently used. When the soluble polypeptide of the present invention or ChM1L is secreted into blood or synovial fluid, the amount the soluble polypeptide of the present invention or ChM1L in body fluid such as blood or serum of the examinee can be measured. The sample can be diluted if necessary with a buffer solution or the like and used in the method of the present invention.

Further, the present invention provides a reagent for a method of diagnosing diseases associated with angiogenesis or bone resorption. That is, the present invention relates to a diagnostic reagent for diseases accompanied by angiogenesis and diseases wherein the activity of ChM1L is reduced or enhanced, for example, cancer, rheumatoid arthritis and tendinitis, which comprises an antibody recognizing a peptide containing the amino acid sequence of the soluble polypeptide of the present invention.

The antibody constituting the reagent of the present invention can be labeled with a suitable label depending on an assay format. Alternatively, the antibody constituting the reagent of the present invention can be immobilized on a suitable support depending on an assay format. The reagent of the present invention can be combined not only with the antibody but also with an additional element necessary for examination and storage to constitute a diagnostic reagent. The additional element which can constitute the kit includes a buffer solution for diluting a reagent and a biological sample, a positive control, a negative control, a substrate for measuring a label, etc. If necessary, these elements can be previously mixed with one another. If necessary, a preservative or an antiseptic can be added to each element. The kit can contain a reaction container, instructions showing an assay protocol, etc.

The diagnosis of disease in the present invention includes, for example, the following diagnosis. Patients with diseases accompanied by angiogenesis or diseases wherein the activity of ChM1L is reduced or enhanced, for example, cancer, rheumatoid arthritis and tendinitis, who cannot be judged by general examinations, can be easily judged by examination based on the present invention. More specifically, an increase or decrease in the expression level of ChM1L protein in a patient with symptoms which may be attributable to tendinitis indicates a high possibility that the cause of the symptoms is tendinitis.

The diagnosis in the present invention also enables measurement to judge whether diseases accompanied by angiogenesis or diseases wherein the activity of ChM1L is reduced or enhanced, for example cancer, rheumatoid arthritis and tendinitis, are ameliorated or not. That is, the present invention is useful for judgment of the therapeutic effect on such diseases. More specifically, an increase or decrease in the expression level of ChM1L protein in a patient with symptoms which may be attributable to tendinitis indicates a high possibility of further progress or amelioration of tendinitis.

On the basis of a difference in the expression level, it is also possible to judge the severity of diseases accompanied by angiogenesis or diseases wherein the activity of ChM1L is reduced or enhanced, for example cancer, rheumatoid arthritis and tendinitis. That is, there is a possibility that the expression level of ChM1L protein is correlated with the severeness of such diseases.

<Pharmaceutical Preparation>

The therapeutic agent for diseases accompanied by angiogenesis or diseases wherein the activity of ChM1L is reduced or enhanced, for example cancer, rheumatoid arthritis and tendinitis (psoriasis, angioma, diabetic retinopathy, corneal damage, or angiogenesis upon corneal transplantation) can be produced by mixing the soluble polypeptide of the invention as an active ingredient with a physiologically acceptable carrier, excipient, diluent etc. The therapeutic agent of the present invention can be administered orally or parenterally for the purpose of ameliorating symptoms.

As the oral agent, a preparation form such as granules powder, tablets, capsules, solvent, emulsion or suspension can be selected. The injection includes a subcutaneous injection, an intramuscular injection, a joint cavity injection and an intraperitoneal injection.

As the administration form in ophthalmic therapy, eye drops, an ointment or a contact lens containing the active ingredient is used. In intravascular topical administration, the active ingredient can be used in a form contained in, or applied onto, a stent or an intravascular embolus agent.

When the active ingredient in a therapeutic agent to be administered consists of a protein, its coding gene can be introduced into the living body by techniques of gene therapy to achieve the therapeutic effect. Techniques for treating diseases by introduction of a gene encoding a protein having therapeutic effect into the living body and expressing therein are known (Kaneda, Nippon Yakuri Zasshi, Vol. 117, pp. 299-306, 2001).

The dose varies depending the age, sex, weight and symptoms of the patient, therapeutic effect, administration method, treatment time, or the type of an active ingredient contained in the pharmaceutical composition, but can be administered usually in the range of 0.1 mg to 500 mg, preferably 0.5 mg to 20 mg, in each administration per an adult. However, the dose varies depending on various conditions, and there are cases where a dose less than the above range may be sufficient or a dose higher than the above range may be necessary.

Hereinafter, the present invention is described in more detail by reference to the Examples, but these examples do not limit the present invention.

Unless otherwise specified, the respective procedures in the following examples were carried out according to methods described by Sambrook J, Fritsch E. F., Maniatis T. in Molecular Cloning: a laboratory Manual, $2^{nd}$ Edn., USA, Cold Spring Harbor Laboratory Press (1989), or when a commercial reagent or kit is used, the commercial product was used according to its instructions.

EXAMPLES

In the following examples, COS7 cells were cells (No. CRL-1651) available from ATCC (American Type Culture Collection) and derived from Africa green monkey kidney; 293T cells are cells (Cat. No. Q401) available from Gene Hunter Co. and derived from human embryonic kidney; MRC-5 cells are cells (No. RCD0211) available from Riken Bio Resource Center and derived from human embryonic normal fibroblasts; B16F10 cells are cells (No. CRL-6475) available from ATCC and derived from mouse melanoma; and Lewis lung carcinomas (LLC) cells are cells (No. CRL-1642) available from ATCC and derived from mouse lung cancer. In the Examples, HUVECs (human umbilical vein endothelial cells) and HMVECs (human dermal micro vascular endothelial cells) are available from Clonetics, and NHDFs are available from Sanko Junyaku.

Example 1

Detection of the Soluble Polypeptide Protein

<Method> A cDNA (SEQ ID NO: 1) encoding a protein having a FLAG tag fused with the C-terminal of human ChM1L (amino acids 1 to 317) was amplified by PCR and cloned into pCAGGS vector (Miwa et al., Gene, Netherlands, Vol. 108, No. 2, pp. 193-200, Dec. 15, 1991) (pCAGGS-hChM1L-FLAG). The FLAG tag (Sigma) described in this example is a hydrophilic marker peptide consisting of 8 amino acids (Asp Tyr Lys Asp Asp Asp Asp Lys (SEQ ID NO: 10)). Using LIPOFECTAMINE™ PLUS REAGENT (Life Technologies) (transfection reagents) according to manufacture's instructions, COS7 cells and 293T cells were transfected with pCAGGS and pCAGGS-hChM1L-FLAG. About 48 hours after transfection, the culture supernatant was recovered and subjected to immunoprecipitation with anti-FLAG M2 agarose (Sigma). After immunoprecipitation, the sample was subjected to SDS-PAGE (sodium dodecyl sulfate-polyacrylamide gel electrophoresis) on 15% gel and transferred onto a nitrocellulose membrane. As a primary antibody, anti-ChM1L polyclonal antibody (Non-patent document 4: Yamana et al., Biochemical and Biophysical Research Communications, USA, Vol. 280. No. 4, pp. 1101-1106, Feb. 2, 2001), and as a secondary antibody, horseradish peroxidase-labeled anti-rabbit IgG antibody (Dako) was used, and coloration reaction was carried out by using ECLPLUS™ reagent (Amersham Pharmacia Biotech) (chemiluminescent western blotting detection reagents)according to manufacture's instructions.

<Results> FIG. 1 shows the results of the soluble polypeptide by Western blotting (lane 1, pCAGGS (COS7 cells); lane 2, pCAGGS-ChM1L-FLAG (COS7 cells); lane 3, pCAGGS (293T cells); and lane 4, pCAGGS-ChM1L-FLAG (293T cells). It was revealed that about 15-kDa soluble polypeptide is present in a culture of the cells transfected with pCAGGS-ChM1L-FLAG.

Example 2

Purification of the Soluble Polypeptide and Analysis of N-terminal Amino Acid Sequence <Method> Using LIPOFECTAMINE™ PLUS REAGENT (Life Technologies) according to manufacturer's instructions, 293T cells were transfected with pCAGGS-hChM1L-FLAG, and after about 48 hours, a culture supernatant was recovered. Anti-FLAG M2 agarose (Sigma) was used to prepare an affinity column, and the culture supernatant was applied onto the column. The column was washed with 25 mM Tris-HCl buffer, 150 mM NaCl (pH 7.4) and subjected to elution with 0.1 M glycine-HCl (pH 3.5), and the eluent was neutralized with a 1/20 volume of 1 M Tris-HCl (pH 9.5). The eluent was subjected to SDS-PAGE on 15% gel, then transferred onto a SEQUI-BLOT™ PVDF membrane (Bio-Rad) (PVDF membrane for blotting) and stained with GELCODE BLUESTAIN REAGENT™ (Pierce) (protein staining reagents). A band of about 15 kDa was cutoff, treated with pyroglutamate aminopeptidase (Takara) and analyzed for N-terminal amino acid sequence by the Edman degradation method.

<Results> Each fraction in the step of purifying the soluble polypeptide was subjected to SDS-PAGE and stained with GELCODE BLUESTAIN REAGENT™ (Pierce) (protein staining reagents), and the results are shown in (A) (lane 1, culture supernatant; lane 2, fraction not absorbed on the column; lane 3, wash fraction; and lanes 4 to 11, elution fractions). It was revealed that about 15-kDa protein is present in the fractions eluted from the column. When the 15-kDa band was cut off and analyzed by the Edman degradation method, its amino acid sequence could not be read, and it was thus estimated that the N-terminal had been blocked. When the protein was treated with pyroglutamate aminopeptidase and then analyzed for the N-terminal amino acid sequence, the N-terminal amino acid sequence was revealed to be a sequence ASEEELP (SEQ ID NO: 11). It was thus revealed that the soluble polypeptide was composed of 81 amino acids (SEQ ID NO: 4) in positions 237 to 317 of membrane-bound ChM1L (317 amino acids), and glutamine at position 237 as the N-terminal amino acid had been converted into pyroglutamic acid (B: see comparison of the cleavage site of ChM1L with that of ChM-I).

Example 3

Expression of MS-ChM1L in *Escherichia coli* and Purification Thereof

<Method> A cDNA (SEQ ID NO: 5) encoding a protein having a methionine-containing His tag and a FLAG tag fused with the N-terminal of a partial amino acid sequence in positions 237 to 317 of human ChM1L was amplified by PCR and then cloned into a PET VECTOR™ (Novagen) (expression vector) (pET-shChM1L). pET-shChM1L was introduced into *Escherichia coli* Origami B (DE3) pLysS (Novagen). The *Escherichia coli* was cultured overnight in LB medium, and a part thereof was cultured again for about 3 hours, followed by adding isopropyl-1-thio-β-D-galactopyranoside (IPTG) at a final concentration of 1 mM to induce expression of the recombinant protein, and the *Escherichia coli* was cultured for additional 4 hours. The culture solution was centrifuged at 5000×g to form a pellet of the *Escherichia coli* which was then lysed with 6 M guanidine, 0.1 M NaH$_2$PO$_4$ in 0.01 M Tris-HCl buffer, pH 8.0, centrifuged to remove an insoluble fraction, and applied to a nickel nitrilotriacetic agarose (Qiagen) column. The column was washed with 0.01 M Tris-HCl buffer, pH 8.0, containing 8 M urea and 0.1 M NaH$_2$PO$_4$ and then washed with the buffer containing imidazole at a gradually increased concentration, and the recombinant protein was eluted with the buffer containing 200 mM imidazole. The eluted fraction was applied to a PD-10™ column (Amersham Pharmacia Biotech) (desalting column), and the buffer was exchanged with 25 mM HEPES, 0.15 M NaCl, pH 8.3. Endotoxin in the recombinant protein solution was removed Triton X-114 by the following method that was a modification to a method of Aida et al. (Journal of Immunological Methods, Netherlands, Vol. 132, No. 2, pp. 191-195, Sep. 14, 1990). Triton X-114 was added at a final concentration of 1% to the recombinant protein solution and incubated for 30 minutes on ice and then at 37° C. for 10 minutes and centrifuged at 2000×g at 25° C. for 10 minutes, to recover a supernatant. Triton X-114 was added at a final concentration of 1% to the supernatant, and the above procedure was repeated once more. The PD-10™ column (Amersham Pharmacia Biotech) (desalting column) was washed with 1% sodium deoxycholate to remove endotoxin from the column, and then the buffer in the column was exchanged with 25 mM HEPES, 0.15 M NaCl, pH 8.3, made free of endotoxin by Posidain Filter (Pole), and then Triton X-114 remaining after application of the recombinant polypeptide solution was removed. The endotoxin concentration was measured by a limulus amebocyte lysate assay (Biowhittacker). The protein concentration was measured by a BCA protein assay reagent (Pierce) by using bovine serum albumin as standard. The purified recombinant polypeptide was subjected to SDS-PAGE on 15% gel and stained with GELCODE BLUESTAIN REAGENT™ (Pierce) (protein staining reagents).

<Results>The results of the purified recombinant polypeptide subjected to SDS-PAGE and stained with GELCODE BLUESTAIN REAGENTTM (Pierce) (protein staining reagents) are shown in FIG. 3 (lane 1, not reduced (−2-mercaptoethanol); lane 2, reduced (+2-mercaptoethanol)). The endotoxin concentration of the purified recombinant polypeptide was less than 5 EU/ml/mg protein, and the yield was 15 to 30 mg/L culture. By the method described above, the recombinant polypeptide capable of administration into cells and the living body could be obtained in a large amount.

Example 4

Analysis of Inhibitory Action on Growth of Vascular Endothelial Cells

<Method>Analysis of cellular growth was carried out with DNA synthesis (incorporation of BrdU into cells) as an indicator. The cells were cultured in a 96-well plate at a density of 3,000 cells/well and then incubated for 24 hours in the absence of serum (37° C., in the presence of CO$_2$). After each well was washed, the cells were stimulated in the presence of a varying concentration of MS-ChM1L with 10 ng/mL FGF-2 (fibroblast growth factor 2), 10 ng/mL VEGF (vascular endothelial growth factor), 10 ng/mL HGF (hepatocyte growth factor) and 10% FBS (fetal bovine serum) for 24 hours (FIGS. 4B to 4E) or 48 hours (FIG. 4A). Incorporation of BrdU into the cells is conducted for the last 3 hours of culture.

<Results> The inhibitory activity of MS-ChM1L on synthesis of DNA in various kinds of cells is shown in FIG. 4. In FIG. 4, A shows that MS-ChM1L inhibits the synthesis of DNA in HUVECs stimulated with the various factors, B shows that MS-ChM1L shows concentration-dependent inhibition of the synthesis of DNA in HUVECs stimulated with FGF-2, C shows that MS-ChM1L inhibits the synthesis of DNA in HMVECs, D shows that MS-ChM1L does not inhibit the synthesis of DNA in NHDFs, and E shows that MS-ChM1L does not inhibit the synthesis of DNA in MRC-5. Each of the respective values is mean±standard deviation, and "" and "*" indicate significant difference relative to the control (vehicle value) (, p<0.01; *, P<0.001).

100 μg/mL MS-ChM1L almost completely inhibited FGF-2-, VEGF-, HGF- and FBS-dependent synthesis of DNA in human umbilical vein endothelial cells (HUVECs, available from Clonetics) (FIG. 4A). Further, MS-ChM1L was observed to exhibit concentration-dependent inhibition of FGF-2-dependent synthesis of DNA (FIG. 4B). The inhibition of DNA synthesis by MS-ChM1L was also observed in other human dermal micro vascular endothelial cells (HMVECs, Clonetics) (FIG. 4C). However, 100 μg/mL MS-ChM1L was not observed to inhibit synthesis of DNA in human fibroblasts, that is, normal human dermal fibroblasts (NHDFs, Sanko Junyaku) and MRC-5 cells (normal lung fibroblasts) (FIGS. 4D and 4E). From the foregoing, it was estimated that MS-ChM1L exhibits vascular endothelial cell-specific inhibition of DNA synthesis.

Example 5

Analysis of Inhibitory Action on Formation of Capillary Tubes by Vascular Endothelial Cells <Method> Growth factor-reduced Matrigel (Becton Dickinson) was added to a 24-well plate in a volume of 320 μL/well and incubated at 37° C. for 30 minutes. A cell suspension containing 50,000 HUVECs/mL was prepared using a medium obtained by diluting EGM-2 medium (Clonetics) in a ratio of 1/8 with EBM-2 medium (Clonetics). 100, 25 or 12.5 μg/mL recombinant MS-ChM1L or a buffer (25 mM HEPES, 0.15 M NaCl, pH 8.3) was added to 1 mL of the cell suspension (50,000 cells) and then seeded on the 24-well plate coated with growth factor reduced Matrigel, and after 6 hours, formation of capillary tubes was observed and photographed.

<Results> FIG. 5 shows that MS-ChM1L inhibits the formation of capillary tubes by HUVECs. In FIG. 5, A indicates formation of capillary tubes in the presence of 25 mM HEPES, 0.15 M NaCl, pH 8.3; B, in the presence of 100 μg/mL MS-ChM1L; C, in the presence of 25 μg/mL MS-ChM1L; D, in the presence of 12.5 μg/mL MS-ChM1L; and the scale bar indicates a length of 100 μm. It was revealed that MS-ChM1L exhibits concentration-dependent inhibition of formation of capillary tubes by HUVECs.

Example 6

Analysis of Inhibitory Action on Migration of Vascular Endothelial Cells

<Method> An experiment of migration of vascular endothelial cells was carried out by using a TRANSWELL™ (Coster) (culture inserts with porous membrane) with a pore size of 8 mm comprising a filter whose upper and lower layers were coated with 1 μg/mL vitronectin (Sigma). That is, 600 μg of a medium containing 0.1% serum, a medium containing 10 ng/mL VEGF or a medium containing 10 ng/mL FGF-2 were added to each well of a 24-well plate. After the filter was fitted to each well of the plate, human umbilical vein endothelial cells (HUVECs, Clonetics) previously cultured in the absence of serum for 24 hours were suspended in a medium containing MS-ChM1L at a varying concentration and then added at a density of 50,000 cells/well onto the upper layer of the filter. After the cells were incubated at 37° C. in the presence of $CO_2$ for 4 hours, the filter was removed and the cells thereon were fixed with methanol. The filter was stained with a Diff-Quick staining solution (Dade Behring), and the cells on the upper layer of the filter were removed with a cotton swab. The filter was cut with a cutter and sealed with a slide glass, and cells that had migrated were counted under a microscope. The number of cells that had migrated was determined per visual region.

<Results> FIG. 6 shows that MS-ChM1L inhibits migration of HUVECs. In FIG. 6, A shows that MS-ChM1L exhibits inhibition of migration of HUVECs toward VEGF, and B shows that MS-ChM1L exhibits concentration-dependent inhibition of migration of HUVECs toward FGF-2. Each of the respective values is mean±standard deviation and indicates significant difference relative to the control (vehicle) value (*, P<0.05; **, P<0.01). As a result of the migration experiment, it was observed that the migration of the cells toward VEGF and FGF-2 is inhibited by MS-ChM1L (FIGS. 6A and 6B). This migration inhibition was strongest in the presence of 100 μg/mL MS-ChM1L, thus indicating concentration-dependent inhibition. That is, MS-ChM1L was revealed to inhibit migration of vascular endothelial cells.

Example 7

Analysis of Inhibitory Action on Adhesion of Vascular Endothelial Cells

<Method> A 96-well plate was coated with 1 μg/mL fibronectin (Sigma), 1 μg/mL vitronectin (Sigma) or 1 μg/mL type I collagen (Sigma). Each well was washed and then blocked with PBS containing 1% BSA. HUVECs were suspended at a density of 1,000,000 cells/mL in a serum-free medium and fluorescence-labeled with CALCEIN™ AM (Molecular Probes) (acetacetoxymethyl ester). The cells were washed and then added to each well at a density of 100,000 cells/well, and MS-ChM1L was added to each well at a concentration of 100 μg/mL. After the cells were incubated at 37° C. in the presence of $CO_2$ for 1 hour, each well was washed and measured for its fluorescence intensity with a fluorescence plate reader.

<Results> FIG. 7 shows that MS-ChM1L inhibits adhesion of HUVVECs to vitronectin. Each of the respective values is mean±standard deviation, and  indicates significant difference relative to the control (vehicle value) value (, P<0.011). The inhibition, by MS-ChM1L, of adhesion of HUVECs to vitronectin was observed. On the other hand, no influence on the adhesion of the cells to fibronectin or type I collagen was observed. That is, it was revealed that MS-ChM1L inhibits adhesion of the cells to vitronectin. It was also revealed that the method of this experiment is a method capable of easily measuring the activity of recombinant MS-ChM1L protein. Further, it was revealed that because vitronectin is known to bind to integrin $\alpha_v\beta_{III}$, MS-ChM1L inhibits the interaction between vitronectin and integrin $\alpha_v\beta_{III}$. In addition, a mechanism was estimated wherein MS-ChM1L binds to integrin $\alpha_v\beta_{III}$ to regulate the activity thereby exhibiting an action of inhibiting angiogenesis.

Example 8

Analysis on Cell Cycle of Vascular Endothelial Cells

<Method> Analysis of cell cycle was carried out by monitoring the amount of DNA in cells by a flow cytometer. The cells proceed regularly in the order of M stage→G1 stage→S stage→G2 stage→(M stage), and the stage of the cells in this cell cycle can be identified by examining the amount of DNA in the cells. HUVECs were cultured at a density of 1,000,000 cells/well in a 10-cm dish and then incubated for 24 hours in the absence of serum (37° C., in the presence of $CO_2$). After washing, the cells were stimulated for 24 hours in the presence of 100 μg/mL MS-ChM1L in EGM-2 medium. The cells were treated with Triton-X100, RNase, then stained with PI (propidium iodide) and analyzed by a flow cytometer.

<Results> As compared with stimulation of the cells with EGM-2 medium only (FIG. 8A), stimulation of the cells with both EGM-2 medium and MS-ChM1L brought about an increased number of cells in the G1 stage and a decreased number of cells in the S stage and G2/M stage (FIG. 8B). This result indicates that the cells in the G1 stage do not proceed to the S stage. Accordingly, it was suggested that the cell cycle of HUVECs is stopped in the G1 stage (G1 arrest) by the action of MS-ChM1L.

Example 9

Analysis on Production of Matrix Metalloproteases (MMPs) in Vascular Endothelial Cells <Method>HUVECs were cultured in a 24-well plate and then incubated for 24 hours in the absence of serum (37° C., in the presence of $CO_2$). After washing, the cells were not stimulated, or stimulated with 10 ng/mL TNF-α for 24 hours, in the presence of 100 μg/mL MS-ChM1L. Total RNA was extracted with RNEASY™ MINI KIT (Qiagen) (RNA extraction regents) and DNase I and subjected to reverse transcription reaction using OMNI-SCRIPT™ RT KIT (Qiagen) (cDNA synthesis kit) to synthesize cDNA. Real-time PCR was carried out in a reaction solution with a total volume of 10 μL containing 0.1 μM each of a sense primer and an antisense primer, 5 μL 2×SYBR GREEN™ PCR MASTER MIX (Applied Biosystems) (premixed reagents for real-time PCT), and 2 μL of the cDNA. The reaction conditions were 1) denaturation (95° C., 15 seconds) and 2) annealing and extension reaction (60° C., 1 minute). Quantification of the expression level of each target gene was carried out by using GeneAmp 5700 Sequence Detection System Software (Applied Biosystems).

Quantification of the amplified PCR product was carried out by measuring the intensity of a fluorescence signal of SYBR GREEN™ (fluorescent dye) bound to the amplified PCR product (double-stranded DNA) with time in each PCR cycle, to form an amplification curve of the PCR product vs. the number of cycles and calculating a threshold cycle (Ct) value at which the amplification curve and an arbitrary threshold value (which is selected usually in the vicinity of a middle point of an exponential amplification region of the amplification curve) intersect. The relative expression level of the target mRNA, relative to 18S as internal standard, was calculated according to equation $2^{-(Ct\ of\ target - Ct\ of\ 18S)}$.

<Results> Expression of MMP-2 mRNA and MT1-MMP mRNA was analyzed. The influence of MS-ChM1L on expression of matrix metalloprotease mRNA in HUVECs is shown in FIG. 9. In FIG. 9, A shows that MS-ChM1L inhibits expression of MMP-2 mRNA, and B shows that MS-ChM1L exhibits expression of MT1-MMP mRNA. Each of the respective values is mean±standard deviation, and * and ** indicate significant difference relative to the control (vehicle) value (*, $p<0.05$; **, $P<0.01$).

It is known that expression of MMP-2 and MT1-MMP is increased when vascular endothelial cells are stimulated with TNF-α (J. Cell Sci., 2001, January; 114 (Pt 1):131-139, Blood., 2003, Mar. 1; 101(5):1810-7, Biochem. J., 1993, Dec. 15; 296 (Pt 3):803-9). Under this experimental condition, an increase in the expression by TNF-α was not recognized, but regardless of whether TNF-α was present or not, MS-ChM1L inhibited expression of MMP-2 mRNA and MT1-MMP mRNA (FIGS. 9A and B).

MMP-2 and MMP-9 are MMPs involved considerably in destruction of basement membrane, and strongly degrade IV type collagen that is a primary component of basement membrane. MT1-MMP not only converts precursor MMP-2 on a cell membrane into activated MMP, but also degrades extracellular matrix. Accordingly, the present results in which the expression of MMP-2 mRNA and MT1-MMP mRNA was inhibited by the action of MS-ChM1L suggest a possibility that MS-ChM1L inhibits destruction of basement membrane upon angiogenesis.

Example 10

Analysis of In Vivo Inhibitory Action on Angiogenesis in FGF-2-Induced Sponge Angiogenesis Model <Method> The in vivo inhibitory action of MS-ChM1L on angiogenesis was examined by using an FGF-2-induced sponge angiogenesis model (Br J Pharmacol. 2000, 399, 2-3, 233-237). A circular sponge disk (thickness 5 mm×diameter 15 mm) was transplanted subcutaneously onto the back of a male SD rat (7-week-old), and for 3 days from the following day, human recombinant FGF-2 (500 ng/50 μL/site) was administered once per day into the sponge to induce angiogenesis. MS-ChM1L (5 μg/50 μL/site) was administered into the sponge once per day for 3 days. On the fourth day, the sponge and its surrounding tissues were excised and examined by observation with the naked eye and by histological examination.

<Results> By administration of FGF-2, formation of granulation tissues and angiogenesis in the granulation tissues around the sponge were observed, and MS-ChM1L significantly inhibited formation of granulation tissues, and angiogenesis in the granulation tissues, in this model (FIG. 10). In this model, active inflammation was observed in an initial stage of the transplantation, and the growth and angiogenesis of the granulation tissues around the sponge were observed. Accordingly, it was suggested that MS-ChM1L inhibits growing inflammation, as well as growth and angiogenesis of granulation tissues.

Example 11

Analysis of Inhibitory Action on Formation of Osteoclasts Examination Using M-CSF-Dependent Bone Marrow Macrophage <Method> Formation of osteoclasts by using M-CSF (macrophage colony stimulating factor)-dependent bone marrow macrophages was carried out by using a partial modification to a method of Azuma et al. (The Journal of Biological Chemistry, USA, Vol. 275, No. 7, pp. 4858-4864, Feb. 18, 2000). Bone marrow cells were removed from femurs and tibias of 7- to 8-week-old male ddY mice (Nippon SLC) and, after bursting of erythrocytes, were cultured in a medium containing α-MEM, 10% FBS, 100 ng/mL human M-CSF (Pepro-Tech EC Ltd.) and subjected twice to subculture to give bone marrow-derived macrophages showing M-CSF-dependent growth. The cells were put to a 48-well plate at a density of 10,000 cells/well, and after 6 hours (confirmation of attachment of the cells to the well), 100 ng/mL human M-CSF, 50 ng/mL human sRANKL (soluble RANK ligand, Pepro-Tech EC Ltd.) and MS-ChM1L or ChM-I were added. After 5 days, tartaric acid-resistant phosphatase (TRAP) staining was carried out.

<Results> MS-ChM1L and ChM-I significantly inhibited formation of osteoclasts expressing TRAP (Nature, 2003, May 15, 423 (6937):337-42, Review) known as a marker of mature osteoclast (FIG. 11).

Example 12

Analysis of Inhibitory Action on Formation of Osteoclasts Examination in a Bone Marrow Cell Culture System <Method> Bone marrow cells were removed from femurs and tibias of 9- to 10-week-old male ddY mice (Nippon SLC) and, after bursting of erythrocytes, were suspended in a medium containing α-MEM, 10% FBS, and put to a 48-well plate at a density of 500,000 cells/well, and after 24 hours, $1,25(OH)_2D_3$ known to induce formation of osteoclasts (Nature, 2003, May 15, 423 (6937):337-42, Review) and MS-ChM1L or ChM-I were added. After 8 days, TRAP staining was carried out.

<Results> FIG. 12 shows that MS-ChM1L and ChM-I inhibit formation of osteoclasts from bone marrow cells. In FIG. 12, A indicates formation of osteoclasts in the presence of $1,25(OH)_2D_3$ ($10^{-8}$ M)+vehicle; B, in the presence of $1,25(OH)_2D_3$ ($10^{-8}$ M)+10 μg/mL MS-ChM1L; C, in the presence of $1,25(OH)_2D_3$ ($10^{-8}$ M)+100 μg/mL MS-ChM1L; D, in the presence of $1,25(OH)_2D_3$ ($10^{-8}$ M)+10 μg/mL ChM-I; and E, in the presence of $1,25(OH)_2D_3$ ($10^{-8}$ M)+25 μg/mL ChM-I. As a result, MS-ChM1L and ChM-I significantly inhibited formation of TRAP-positive osteoclasts (FIG. 12).

Example 13

Analysis of Mechanism of Inhibitory Action on Formation of Osteoclasts

<Method> M-CSF-dependent bone marrow macrophage cells prepared in the same method as in Example 11 were put to a 96-well plate at a density of 10,000 cells/well, and after about 6 hours (confirmation of adhesion of the cells to the well), 100 ng/mL human M-CSF, 50 ng/mL human sRANKL (soluble RANK ligand, Pepro-Tech EC Ltd.) and MS-ChM1L were added. MS-ChM 1L was used in treatment in 3 periods of time, that is, Day 0-5, Day 0-3 and Day 3-5. After 5 days, osteoclasts were identified by staining with tartaric acid-resistant phosphatase (TRAP), and the number of formed osteoclasts was examined. Before treatment with MS-ChM1L and 1, 3 and 5 days after the treatment, the medium was removed and total RNA was extracted with RNEASY™ MINI KIT (QIAGEN) (RNA extraction reagents) and RNase-Free DNase Set (QIAGEN). Subsequently, the total RNA was subjected to reverse transcription reaction using OMNISCRIPT™ RT KIT (QIAGEN) (cDNA synthesis kit), to synthesize cDNA. Real-time PCR was carried out with ABI PRISM™ 7000 (Applied Biosystems) using SYBR GREEN™ PCR MASTER MIX (Applied Biosystems) (premixed reagents for real-time PCR) and primers shown below. Primer Rodent GAPDH primer was purchased from Applied Biosystems.

As shown below, each gene measured is known to participate considerably in differentiation and maturation of osteoclasts.

Calcitonin receptor (CTR) is known as a marker of mature multinuclear osteoclasts (Nature, 423(6937):337-42, May 15, 2003, Review). M-CSF is a cytokine essential for survival of osteoclast precursor cells, and its receptor is c-fms (Nature, 423(6937):337-42, May 15, 2003, Review). RANKL is a cytokine essential for formation and activation of osteoclasts, and its receptor is RANK (Nature, 423(6937):337-42, May 15, 2003, Review). NFATc1 is a transcription factor essential for formation of osteoclasts, and it is known that when the function of NFATc1 is inhibited, osteoclasts are not formed (Nature, 423(6937):337-42, May 15, 2003, Review; Dev. Cell., 2002, Dec. 3(6):889-901).

```
CTR
F5'-GTGCTCCTCGGGCTGTAGC         (SEQ ID NO: 12)
R5'-GAGGATTCCGTGGTTCCTGAT       (SEQ ID NO: 13)

TRAP
F5'-GATCCCTCTGTGCGACATCA        (SEQ ID NO: 14)
R5'-CCAGGGAGTCCTCAGATCCA        (SEQ ID NO: 15)

c-fms
F5'-TGGCATCTGGCTTAAGGTGAA       (SEQ ID NO: 16)
R5'-GAATCCGCACCAGCTTGCTA        (SEQ ID NO: 17)

RANK
F5'-ATGAGTACACGGACCGGCC         (SEQ ID NO: 18)
R5'-GCTGGATTAGGAGCAGTGAACC      (SEQ ID NO: 19)

NFATc1
F5'-AGGCTGGTCTTCCGAGTTCA        (SEQ ID NO: 20)
R5'-ACCGCTGGGAACACTCGAT         (SEQ ID NO: 21)
```

<Results> When the M-CSF-dependent bone marrow cells were cultured for 5 days in the presence of 10, 25 or 50 μg/mL MS-ChM1L in an osteoclast forming system on which M-CSF and RANKL were allowed to act, formation of osteoclasts was significantly inhibited by 25 or 50 μg/mL MS-ChM1L (FIG. 13). When MS-ChM1L was allowed to act at an early stage (first to third days) of culture, osteoclasts were not formed by culture even after removal of MS-ChM1L, while when MS-ChM1L was added in a later stage (third to fifth days) of culture, osteoclasts were formed. From these results, it was revealed that MS-ChM1L when allowed to act in an early stage of differentiation of osteoclasts inhibits differentiation of osteoclasts thereafter, but does not inhibit formation of osteoclasts that have been differentiated to a certain degree. Expression of the calcitonin receptor (CTR) known as an osteoclast marker and tartaric acid-resistant phosphatase (TRAP) was inhibited by treatment with MS-ChM1L. Expression of NFATc1 and RANK, that is, factors essential for formation of osteoclasts, was also significantly inhibited. On the other hand, no significant difference was recognized in expression of c-fms, that is, a receptor of M-CSF as a factor essential for survival of osteoclast precursor cells (FIG. 14).

From the foregoing, it was revealed that MS-ChM1L inhibits formation of osteoclasts without inhibiting a survival signal of osteoclasts.

Example 14

Analysis of the Inhibitory Action of Administered MS-ChM1L on Growth of B16F10 Melanoma <Method> B16F10 cells were transplanted subcutaneously into the backs of C57BL6/J mice (male, 6-week-old) at a density of 500,000 cells/mouse, and after 3 days, the tumor size was measured and grouped. After grouping, MS-ChM1L (3 mg/mL) or the vehicle (25 mM HEPES, 0.15 M NaCl, pH 8.3) was administered subcutaneously in an amount of 50 μL/site once per day into a site around the cancer cells. The size of the cancer cells was measured every day with a caliper (length×width$^2$×0.52). Analysis of in vitro growth of B16F10 cells was carried out with DNA synthesis (incorporation of BrdU into cells) as an indicator. The cells were cultured in a 96-well plate at a density of 3,000 cells/well and then incubated for 24 hours in the absence of serum (37° C., in the presence of $CO_2$). After each well was washed, the cells were stimulated with 10% FBS for 24 hours in the presence of a varying concentration of MS-ChM1L. Incorporation of BrdU into the cells is conducted for the last 3 hours of culture.

<Results> MS-ChM1L inhibited growth of B16F10 cells in vivo (FIG. 15A, C). On the other hand, growth of B16F10 cells was not inhibited in vitro (FIG. 15B). From this result, it was estimated that MS-ChM1L inhibited growth of B16F10 cells in vivo by its inhibitory action on angiogenesis.

Example 15

Analysis of the Inhibitory Action of Administered MS-ChM1L on Metastasis of B16F10 Melanoma to the Lung <Method> B16F10 cells were administered intravenously into C57BL6/J mice (male, 6-week-old) at a density of 50,000 cells/mouse, and MS-ChM1L (3 mg/mL) or the vehicle (25 mM HEPES, 0.15 M NaCl, pH 8.3) was administered once per day subcutaneously into the backs of the mice in a dose of 50 µL/site (150 µg/site). The lung was removed 21 days after the transplantation, and the colony cells that had been transferred thereto were counted under a microscope.

<Results> MS-ChM1L inhibited the metastasis of B16F10 cells to the lung (FIG. 16). Each of the respective values is mean±standard deviation, and *** indicates significant difference relative to the control (vehicle) value (P<0.001).

Example 16

Analysis of Action on Induction of Apoptosis of Vascular Endothelial Cells

<Method> It is known that in an initial stage of apoptosis, the structure of a cell membrane is changed such that in normal cells, phosphatidyl serine localized in the inside of a lipid bilayer is exposed to the outside of the cell membrane. Accordingly, analysis of apoptosis-inducing action was carried out by a method of utilizing the binding of annexin V to phosphatidyl serine. Specifically, human dermal micro vascular endothelial cells (HMVECs) were cultured in a 6-well plate at a density of 100,000 cells/well and then incubated for 24 hours in the absence of serum (37° C., in the presence of $CO_2$). After each well was washed, the cells were stimulated with 10 ng/mL FGF-2 in the presence of a varying concentration of MS-ChM1L. After 48 hours, the cells were released with trypsin-EDTA, stained with Annexin V-FITC Apoptosis Detection Kit (Bio Vision) and analyzed by a flow cytometer.

<Results> MS-ChM1L exhibited concentration-dependent induction of apoptosis of HMVECs. From this result, it was estimated that MS-ChM1L has an action of inducing the apoptosis of vascular endothelial cells (FIG. 17). Each of the respective values is mean±standard deviation, and *** indicates significant difference relative to the control (vehicle) value (P<0.001).

Example 17

Detection of Soluble MS-ChM1L Protein in Biological Tissues

<Method> Achilles' tendons, eyeballs, kidneys and livers were removed from DBA1/J mice (male, 13-week-old), then frozen with liquid nitrogen and milled with a pestle in a mortar. Each kind of tissue thus milled was solubilized with 4 M guanidine, 50 mM sodium acetate, pH 5.8 with a homogenizer, then sonicated, and centrifuged at 15,000 rpm for 10 minutes. To the supernatant after centrifugation was added a 9-fold volume of 100% ethanol, and then the supernatant was left at −80° C. for 5 minutes and then centrifuged at 15,000 rpm for 10 minutes. The supernatant was discarded and the precipitates were suspended in 50 mM sodium acetate, pH5.8, followed by adding a 9-fold volume of 100% ethanol and subsequent centrifugation at 15,000 rpm for 10 minutes. The precipitates were solubilized with 8 M urea in 20 mM Tris, pH 8.0. The protein concentration was measured with a BCA protein assay reagent (Pierce) using bovine serum albumin as standard. The sample was transferred onto a nitrocellulose membrane by subjecting it in an amount of 35 µg/lane to SDS-PAGE on 10 to 20% gel. The primary antibody used was an anti-ChM1L polyclonal antibody (Shukunami et al., Biochemical and Biophysical Research Communications, USA, Vol. 280, No. 5, pp. 1323-1327, Feb. 2, 2001), and the secondary antibody used was a horseradish peroxidase-labeled anti-rabbit IgG antibody (Dako), and coloration reaction was carried out by using an ECLPLUS™ reagent (Amersham Pharmacia Biotech) (chemiluminescent western blotting detection reagents) according to manufacture's instructions.

<Results> It was revealed that about 40-kDa membrane-bound ChM1L protein is present in the tendon and eyeball, and about 14-kDa soluble MS-ChM1L protein is present in the tendon (FIG. 18). From the above result, it was revealed for the first time that the soluble MS-ChM1L protein is physiologically present.

Example 18

Analysis of Tissue Specificity of ChM1L mRNA Expression

<Method> Tissue specificity of ChM1L mRNA expression was analyzed by real-time PCR of total RNA extracted from each kind of mouse tissue. That is, the analysis was carried out by the following procedures. Total RNA was extracted from each kind of tissue of C57/BL6 mouse with ISOGEN (manufactured by Nippon Gene) (RNA extraction reagents) and then cleaned up with RNeasy Mini Kit (manufactured by Qiagen) and RNase-Free DNase Set (manufactured by Qiagen). Synthesis of cDNA was carried out by reverse transcription reaction using OMNISCRIPT™ RT KIT (manufactured by Qiagen) cDNA synthesis kit), RNase OUT Recombinant Ribonuclease Inhibitor (manufactured by Invitrogen) and Random Primer (manufactured by Takara Bio). Real-time PCR was carried out by using a reaction solution containing sense and antisense primers for mouse ChM1L gene, SYBR GREEN™ PCR MASTER MIX (Applied Biosystems) (premixed reagents for real-time PCR), and the cDNA. As the primers for measurement of mouse ChM1L mRNA, 5'-AAACACTTCTGGCCCGAGGTAT-3' (SEQ ID NO: 22) (sense primer) and 5'-AGTGTGCTCCATGTCATAG-GTTTTC-3' (SEQ ID NO: 23) (antisense primer) were used. Sense and antisense primers used for measurement of mouse GAPDH mRNA were those purchased from Applied Biosystems. The PCR reaction involved 40 cycles each consisting of 1) denaturation (95° C., 15 seconds) and 2) annealing and extension reaction (60° C., 1 minute). Quantification of the expression level of each target gene was carried out by using GeneAmp 5700 Sequence Detection System software (Applied Biosystems). That is, the expression level was quantified by measuring the intensity of a fluorescence signal of SYBR GREEN™ (fluorescent dye) bound to the amplified PCR product with time in each PCR cycle, to form an amplification curve of the PCR product vs. the number of cycles and calculating a threshold cycle (Ct) value at which the amplification curve and an arbitrary threshold value (selected in the vicinity of a middle point of an exponential amplification region of the amplification curve) intersect. The relative expression level of ChM1L mRNA, relative to GAPDH as internal standard, was calculated according to the following equation:

$$\text{Relative expression level of ChM1L mRNA} = 2^{(Ct\ of\ GAPDH - Ct\ of\ ChM1L)}$$

<Results> Expression of ChM1L mRNA was highest in the Achilles' tendon (FIG. 19). Expression of ChM1L mRNA was also observed in the eye, brain, lung, thymus, diaphragm, stomach, pancreas, muscle, skin and rib, but was considerably lower than in the Achilles' tendon. Expression of ChM1L mRNA was not detected in the spleen, heart, liver, kidney, small intestine and adipose tissue. These results suggested tendon-specific expression of ChM1L.

Example 19

Isolation of Mouse Tendon Cells and Analysis of Cell Specificity of ChM1L mRNA Expression <Method> Mouse tendon cells were isolated by the following procedures. That is, a mouse Achilles' tendon was excised so as not to be contaminated with skin, muscle and fat and digested for 3 hours with 2 mg/mL collagenase in DMEM/10% FBS (37° C., 5% $CO_2$). After centrifugation, the resulting cell pellet was suspended in DMEM/10% FBS and cultured in a 10-cm Petri dish (37° C., 5% $CO_2$). After 7 days, sufficient growth of the cultured cells was observed, and thus the cells were subjected to subculture and used as mouse tendon cells.

<Method> Cell specificity of ChM1L mRNA expression was analyzed by real-time PCR of total RNA extracted from the mouse tendon cells and mouse-derived cell strains. That is, the analysis was carried out by the following procedures. Total RNA was extracted with RNEASY™ MINI KIT (manufactured by Qiagen) (RNA extraction reagents) and RNase-Free DNase Set (manufactured by Qiagen). Synthesis of cDNA was carried out by reverse transcription reaction using OMNISCRIPT™ RT KIT (manufactured by Qiagen) (cDNA synthesis kit), RNaseOUT Recombinant Ribonuclease Inhibitor (manufactured by Invitrogen) and Random Primer (manufactured by Takara Bio). Real-time PCR was carried out by using a reaction solution containing sense and antisense primers for mouse ChM1L gene, SYBR GREEN™ PCR MASTER MIX (Applied Biosystems) (premixed reagents for real-time PCR), and cDNA. As the primers for measurement of mouse ChM1L mRNA, 5'-AAACACT-TCTGGCCCGAGGTAT-3' (SEQ ID NO: 22) (sense primer) and 5'-AGTGTGCTCCATGTCATAGGTTTTC-3' (SEQ ID NO: 23) (antisense primer) were used. Sense and antisense primers used for measurement of mouse GAPDH mRNA were those purchased from Applied Biosystems. The PCR reaction involved 40 cycles each consisting of 1) denaturation (95° C., 15 seconds) and 2) annealing and extension reaction (60° C., 1 minute). Quantification of the expression level of each target gene was carried out by using GeneAmp 5700 Sequence Detection System software. That is, the expression level was quantified by measuring the intensity of a fluorescence signal of SYBR GREEN™ (fluorescent dye) bound to the amplified PCR product with time in each PCR cycle, to form an amplification curve of the PCR product vs. the number of cycles and calculating a threshold cycle (Ct) value at which the amplification curve and an arbitrary threshold value (selected in the vicinity of a middle point of an exponential amplification region of the amplification curve) intersect. The relative expression level of ChM1L mRNA, relative to GAPDH as internal standard, was calculated according to the following equation:

$$\text{Relative expression level of ChM1L mRNA} = 2^{(Ct\ of\ GAPDH - Ct\ of\ ChM1L)}$$

<Results> Expression of ChM1L mRNA in the mouse tendon cells was considerably higher than in other mesenchyme-derived cell lines (FIG. 20). This result suggested tendon cell-specific expression of ChM1L.

Example 20

Examination of the Action of MS-ChM1L on Tumor Angiogenesis

<Method> The action of soluble MS-ChM1L on tumor angiogenesis was analyzed by excising cancer tissues from the mouse transplanted with the B16-F10 cells described in Example 14 and detecting vascular endothelial cells by immune staining. That is, the action of soluble MS-ChM1L was analyzed by the following procedures. Cancer tissues were excised from the mice into which the vehicle and soluble MS-ChM1L had been administered, and then fixed with 4% paraformaldehyde. These were embedded in a usual manner in paraffin to prepare sections. For detection of vascular endothelial cells, rabbit anti-von Willebrand factor (vWF) Ab (manufactured by CHEMICON) and rat anti-mouse CD34 mAb (manufactured by Hycult Biotechnology) were used as the primary antibody. Paraffin of the sections was removed with xylene/alcohol, and then the primary antibody, biotin-labeled secondary antibody, and peroxidase-labeled streptavidin were added. Finally, 3-amino-9-ethylcarbazole (AEC) (manufactured by Nichirei) was added and comparative staining with hematoxylin was carried out, and a typical image was photographed.

By observing the section stained with vWF Ab under a microscope, the number of blood vessels in the cancer tissue was quantified. That is, the section was observed with low magnifying power, and 3 fields with the largest number of blood vessels were selected, and the blood vessels in each field were counted with high magnifying power. The data was indicated as blood vessels/hpf (high power field) by calculating the mean of the 3 fields.

<Results> In the MS-ChM1L administration group, vascular endothelial cells in vWF- and CD34-positive tumors were decreased (FIG. 21A, B). From these results, it was estimated that MS-ChM1L inhibited in vivo growth of cancer cells by its inhibitory action on angiogenesis.

Example 21

Analysis of the Inhibitory Action of Administered MS-ChM1L on Growth of Lewis Lung Carcinomas (LLC)

<Method> LLC cells (ATCC No. CRL-1642) were transplanted subcutaneously into the backs of C57BL6/J mice (male, 6-week-old) at a density of 500,000 cells/mouse, and after 3 days, the tumor size was measured and grouped. After grouping, recombinant human MS-ChM1L (3 mg/mL) or the vehicle (25 mM HEPES, 0.15 M NaCl, pH 8.3) was administered subcutaneously in an amount of 50 µL/site once per day into a site around the cancer cells. The size of the cancer cells was measured every day with a caliper (length×width$^2$× 0.52). Analysis of in vitro growth of LLC cells was carried out with DNA synthesis (incorporation of BrdU into cells) as an indicator. The cells were cultured in a 96-well plate at a density of 3,000 cells/well and then incubated for 24 hours in the absence of serum (37° C., in the presence of $CO_2$). After each well was washed, the cells were stimulated with 10%

FBS for 24 hours in the presence of a varying concentration of MS-ChM1L. Incorporation of BrdU into the cells is conducted for the last 3 hours of culture.

<Results> MS-ChM1L inhibited growth of LLC cells in vivo (FIG. 22A). On the other hand, growth of LLC cells was not inhibited in vitro (FIG. 22B). From these results, it was estimated that MS-ChM1L inhibited growth of LLC cells in vivo by its inhibitory action on angiogenesis.

Example 22

Analysis of Caspase-mediated Action on Induction of Apoptosis of Vascular Endothelial Cells <Method> Caspase is a cysteine protease having a cysteine residue in active center, which is a known key mediator in apoptosis. Analysis of caspase-mediated apoptosis-inducing action was carried out with CaspACE FITC-VAD-FMK In Situ Marker (manufactured by Promega). It is known that CaspACE FITC-VAD-FMK In Situ Marker is a cell-permeable FITC-labeled caspase inhibitor VAD-FMK (FITC-VAD-FMK) which can freely move inside and outside cells and is retained in only apoptosis cells by irreversibly binding to activated caspase. Accordingly, cells undergoing caspase-mediate apoptosis are observed as those having strong fluorescence intensity with FITC by analysis with a flow cytometer. HUVECs at a density of 155,000 cells/well and MRC-5 cells (Institute of Physical and Chemical Research, Bio Resource Center No. RCD02111) at a density of 100,000 cells/well were cultured respectively in 6-well plates and then incubated for 24 hours in the absence of serum (37° C., in the presence of $CO_2$). After each well was washed, the cells were stimulated with 10 ng/mL FGF-2 in the presence of 25 μg/mL MS-ChM1L. After 48 hours, FITC-VAD-FMK was added at a concentration of 10 μM and incubated for 30 minutes (37° C., in the presence of $CO_2$). The cells were released with trypsin-EDTA and analyzed by a flow cytometer.

<Results> MS-ChM1L induced caspase-mediated apoptosis in HUVECs. On the other hand, caspase-mediated apoptosis was not observed in MRC-5 cells (FIG. 23). From these results, it was estimated that MS-ChM1L has a caspase-mediated apoptosis-inducing action specific to vascular endothelial cells.

Example 23

Expression of ChM-I Protein in *Escherichia coli* and Purification Thereof

<Method> A cDNA (SEQ ID NO: 7) encoding a protein having methionine, 6 histidine residues (His tag) and a FLAG tag fused with the N-terminal of human ChM-I was amplified by PCR and then cloned into a PET VECTOR™ (Novagen) (expression vector) (pET-shChM-I). pET-shChM-I was introduced into *Escherichia coli* Origami B (DE3) pLysS (Novagen). The *Escherichia coli* was cultured overnight in LB medium, and a part thereof was cultured again for about 3 hours, followed by adding IPTG at a final concentration of 1 mM to induce expression of the recombinant protein, and the *Escherichia coli* was further cultured for additional 4 hours. The culture was centrifuged at 5000×g to form a pellet of the *Escherichia coli* which was then lysed with 6 M guanidine, 0.1 M $NaH_2PO_4$ in 0.01 M Tris-HCl buffer, pH 8.0, centrifuged to remove an insoluble fraction, and applied to a nickel nitrilotriacetic agarose (Qiagen) column. The column was washed with 0.01 M Tris-HCl buffer, pH 8.0, containing 8 M urea and 0.1 M $NaH_2PO_4$ and then washed with the buffer containing imidazole at a gradually increased concentration, and the recombinant protein was eluted with the buffer containing 200 mM imidazole. The eluted fraction was applied to a PD-10™ column (Amersham Pharmacia Biotech) (desalting column), and the buffer was exchanged with 25 mM HEPES, 0.15 M NaCl, pH 8.3. Endotoxin in the recombinant protein solution was removed with Triton X-114 by the following method that was a modification to a method of Aida et al. (Journal of Immunological Methods, Netherlands, Vol. 132, No. 2, pp. 191-195, Sep. 14, 1990). Triton X-114 was added at a final concentration of 1% to the recombinant protein solution and incubated for 30 minutes on ice and then at 37° C. for 10 minutes and centrifuged at 2000×g at 25° C. for 10 minutes, to recover a supernatant. Triton X-114 was added at a final concentration of 1% to the supernatant, and the above procedure was repeated once more. The PD-10™ column (Amersham Pharmacia Biotech) (desalting column) was washed with 1% sodium deoxycholate to remove endotoxin from the column, and then the buffer in the column was exchanged with 25 mM HEPES, 0.15M NaCl, pH 8.3, made free of endotoxin by Posidain Filter (Pole), and then Triton X-114 remaining after application of the recombinant polypeptide solution was removed. The endotoxin concentration was measured by a limulus amebocyte lysate assay (Biowhittacker). The protein concentration was measured by a BCA protein assay reagent (Pierce) by using bovine serum albumin as standard. The purified recombinant polypeptide was subjected to SDS-PAGE on 15% gel and stained with GELCODE BLUESTAIN REAGENT™ (Pierce) (protein staining reagents).

<Results> The results of the purified recombinant ChM-I protein subjected to SDS-PAGE and stained with GELCODE BLUESTAIN REAGENT™ (Pierce) (protein staining reagents) are shown in FIG. 24 (lane 1, not reduced (−2-mercaptoethanol); lane 2, reduced (+2-mercaptoethanol)). The endotoxin concentration of the purified recombinant ChM-I protein was less than 5 EU/ml/mg protein, and the yield was 10 to 20 mg/L culture. The recombinant ChM-I protein could be obtained by the same method as for the above-described MS-ChM1L.

BRIEF DESCRIPTION OF DRAWINGS

The patent or application file contains at least one drawing executed in color. Copies of this patent or patent application publication with color drawings will be provided by the Office upon request and payment of the necessary fee.

FIG. 4 shows the DNA synthesis inhibitory activity of MS-ChM1L on each kind of cell.

FIG. 22 shows an analysis result of the inhibitory action of administered MS-ChM1L on growth of LLC cells, wherein the growth of LLC is inhibited in vivo by administration of MS-ChM1L, whereas MS-ChM1L does not inhibit in vitro growth of LLC.

SEQUENCE LISTING

Figure 1:
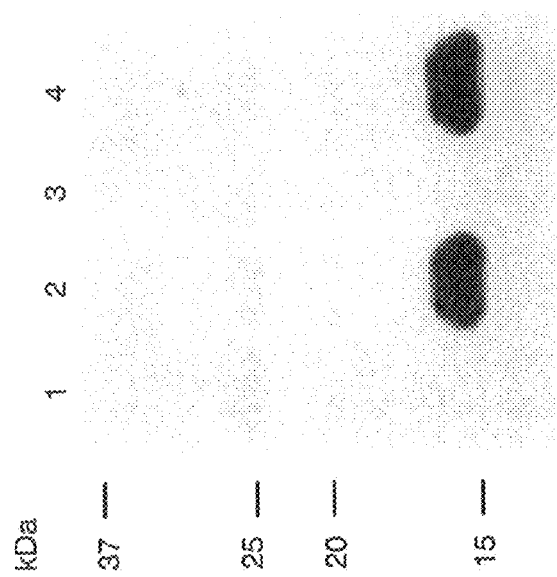
FIG. 1 shows a result of detection of the soluble polypeptide by Western blotting.
Figure 2:
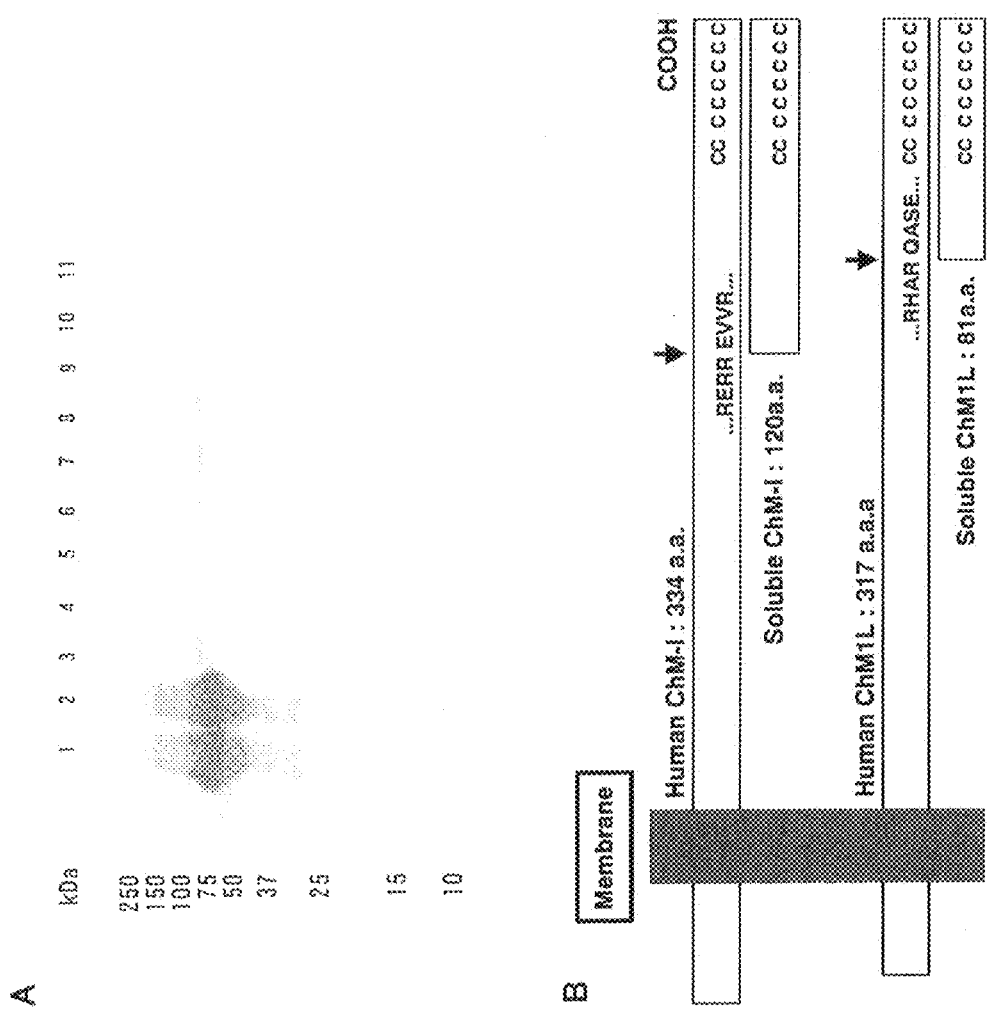
FIG. 2 shows (A) a result of SDS-PAGE, and subsequent staining with GELCODE BLUESTAIN REAGENT™ (Pierce) (protein staining reagents), of each fraction in a process of purifying the soluble polypeptide and (B) comparison of cleavage site between ChM1L and ChM-I.
Figure 3:
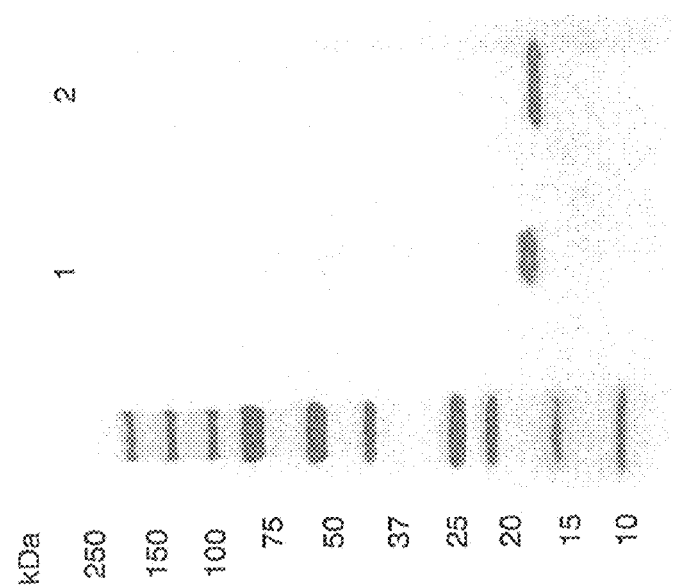
FIG. 3 shows (A) a result of SDS-PAGE, and subsequent staining with GELCODE BLUESTAIN REAGENT™ (Pierce) (protein staining reagents), of purified recombinant MS-ChM1L protein.
Figure 5:
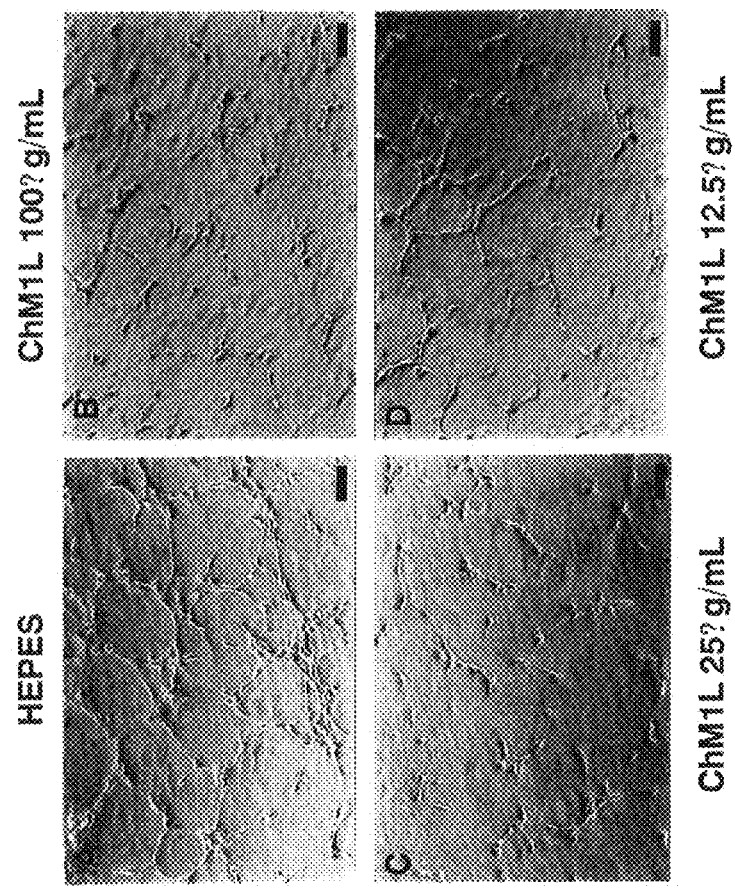
FIG. 5 shows that MS-ChM1L inhibits formation of capillary tubes by HUVECs.
Figure 6B:
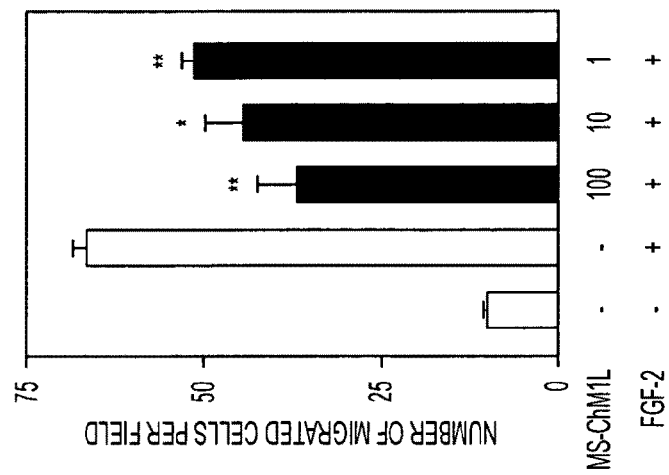
FIG. 6 shows that MS-ChM1L inhibits migration of HUVECs.
Figure 6A:
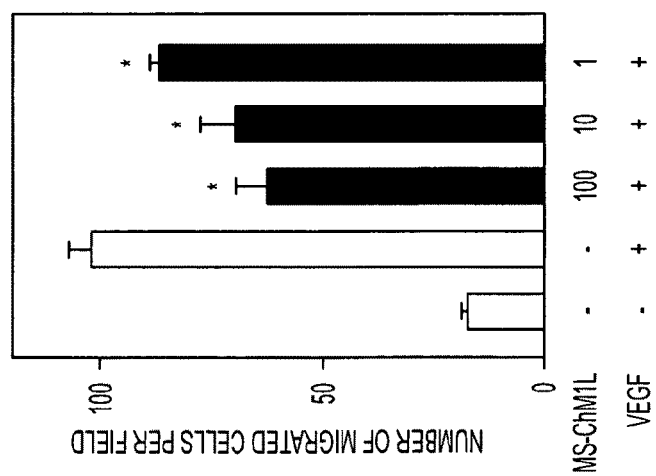
Figure 7:
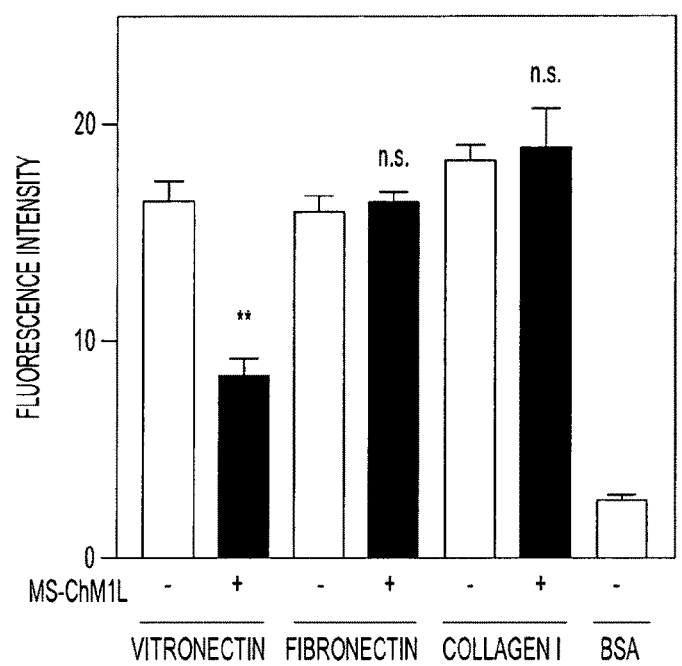
FIG. 7 shows that MS-ChM1L inhibits adhesion of HUVECs to vitronectin.
Figures 8A, 8B:
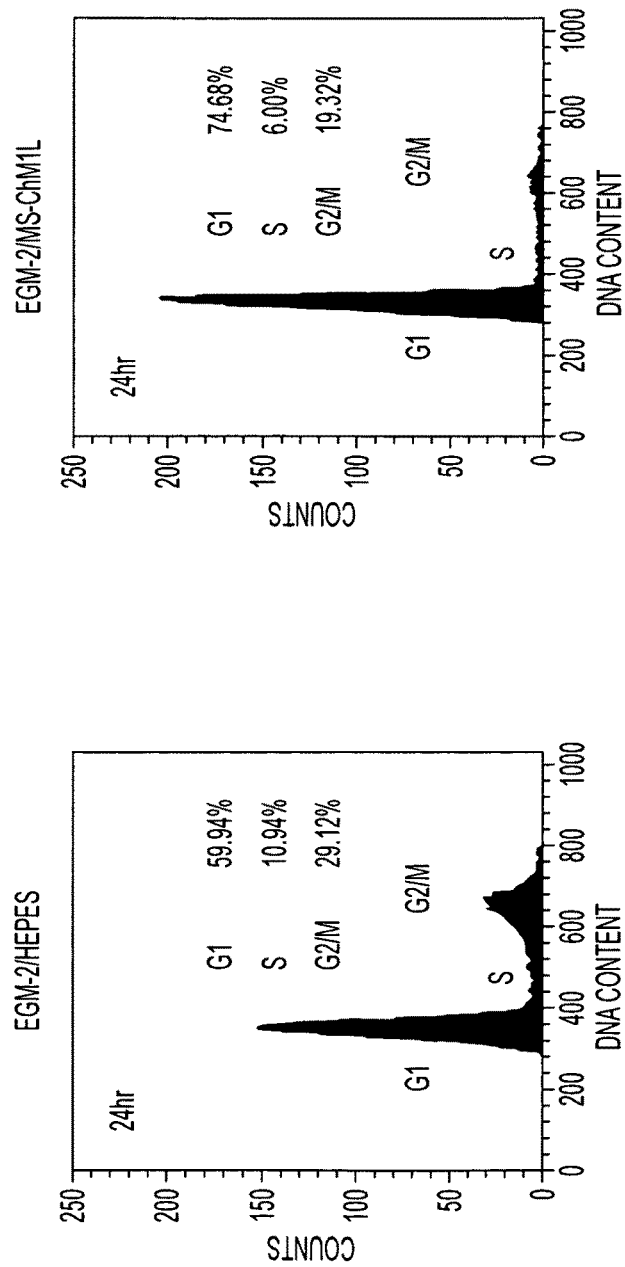
FIG. 8 shows that MS-ChM1L ceases the cell cycle of HUVECs at G1 stage (A, 25 mM HEPES, 0.15 M NaCl, pH 8.3; B, MS-ChM1L 100 μg/mL).
Figure 9A:
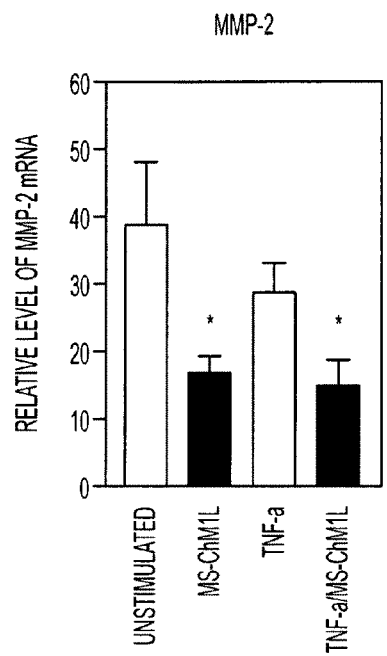
FIG. 9 shows the influence of MS-ChM1L on expression of matrix metalloprotease mRNA in HUVECs.
Figure 9B:
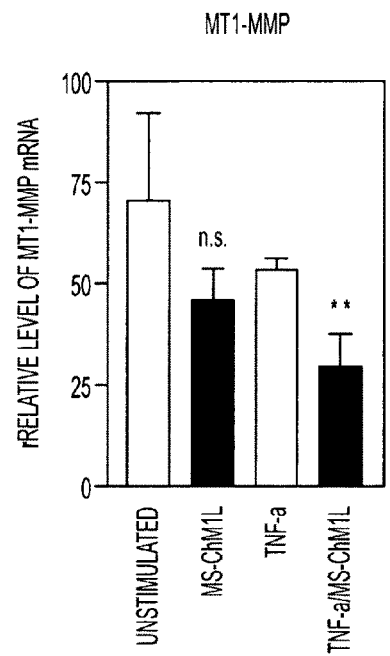
Figure 10:
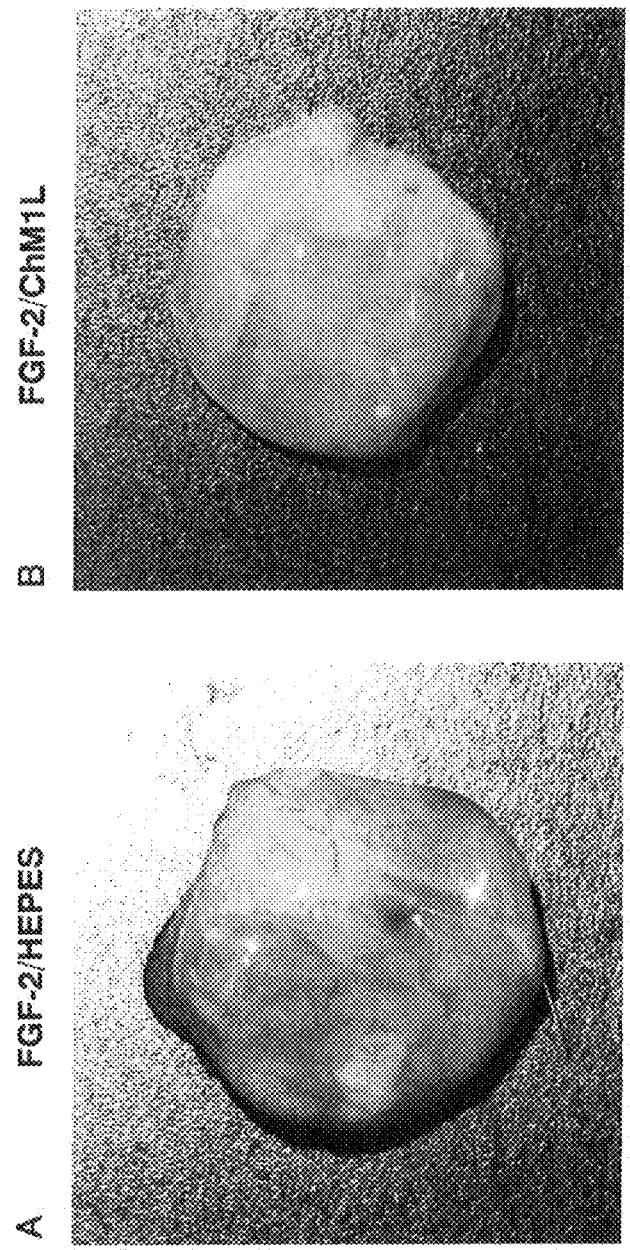
FIG. 10 shows that MS-ChM1L inhibits angiogenesis in vivo in a model having FGF-2-induced granuloma (A, 25 mM HEPES, 0.15 M NaCl, pH 8.3; B, MS-ChM1L 100 µg/mL).
Figure 11:
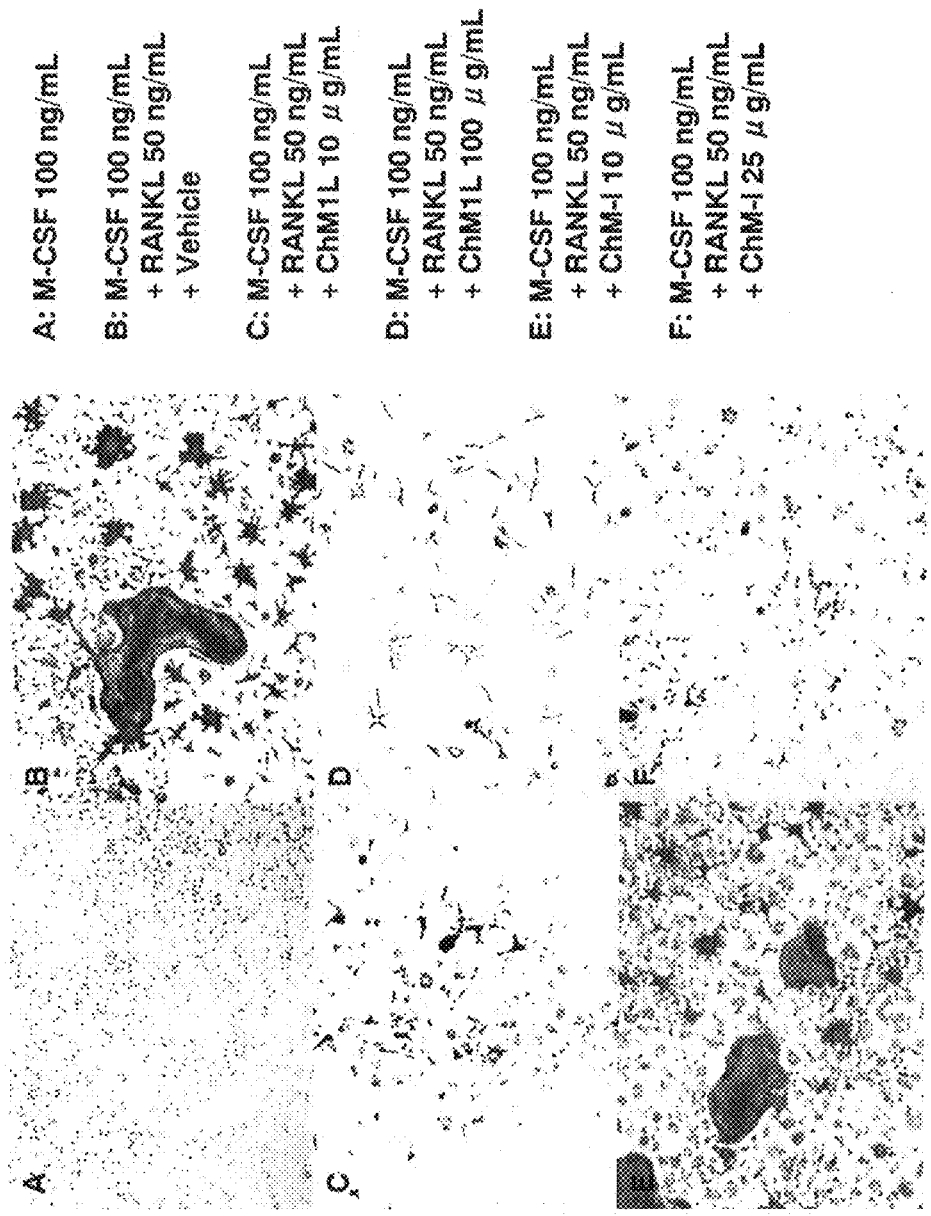
FIG. 11 shows that MS-ChM1L and ChM-I inhibit formation of osteoclasts from M-CSF-dependent bone marrow macrophages (A, M-CSF 100 ng/mL; B, M-CSF 100 ng/mL+ RANKL 50 ng/mL+vehicle; C, M-CSF 100 ng/mL+RANKL 50 ng/mL+MS-ChM1L 10 µg/mL; D, M-CSF 100 ng/mL+ RANKL 50 ng/mL+MS-ChM1L 100 µg/mL; E, M-CSF 100 ng/mL+RANKL 50 ng/mL+ChM-I 10 µg/mL; F, M-CSF 100 ng/mL+RANKL 50 ng/mL+ChM-I 25 µg/mL).
Figure 12:
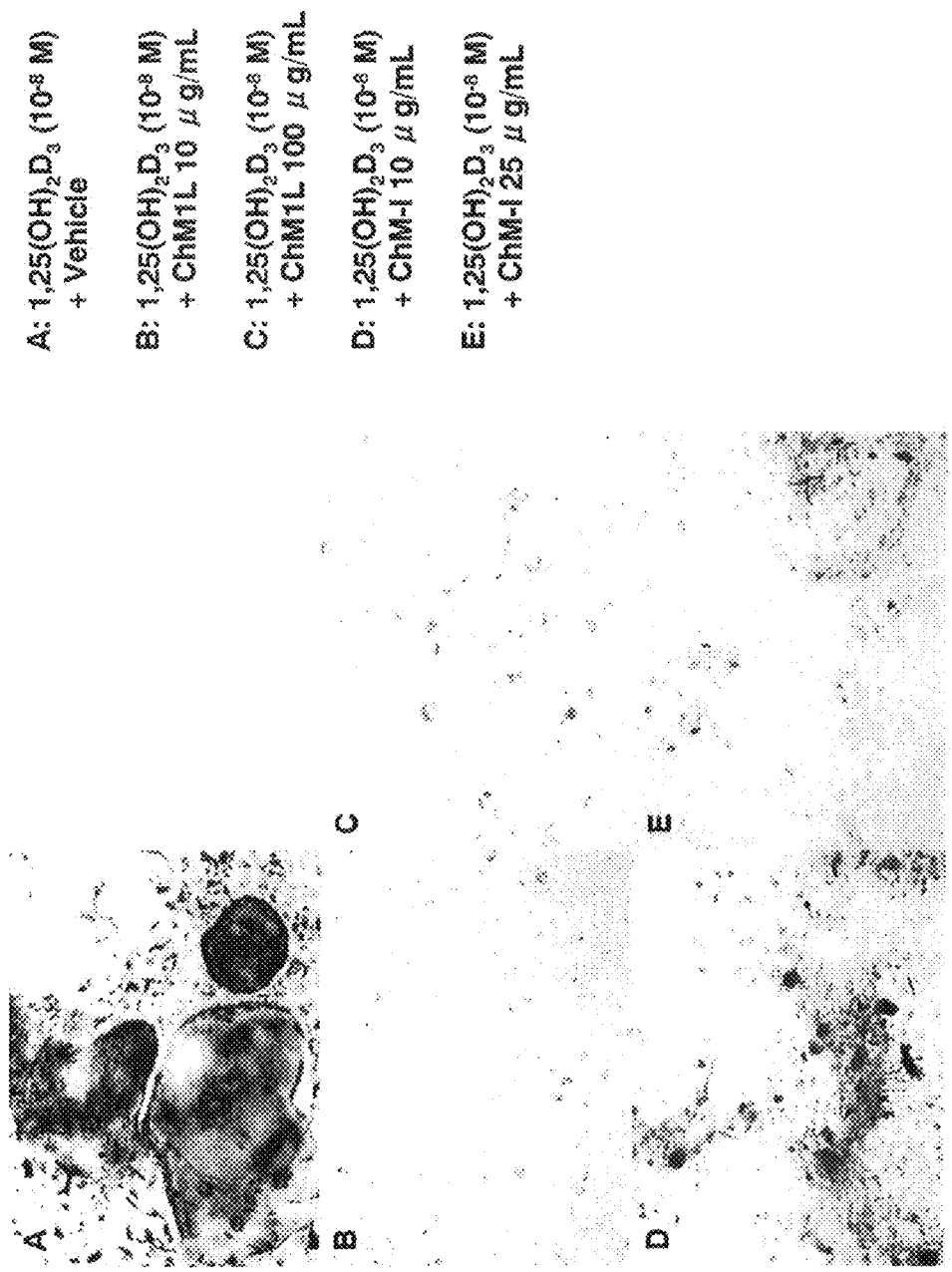
FIG. 12 shows that MS-ChM1L and ChM-I inhibit formation of osteoclasts from bone marrow cells (A, $1,25(OH)_2D_3$ ($10^{-8}$ M)+vehicle; B, $1,25(OH)_2D_3$ ($10^{-8}$ M)+MS-ChM1L 10 µg/mL; C, $1,25(OH)_2D_3$ ($10^{-8}$ M)+MS-ChM1L 100 µg/mL; D, $1,25(OH)_2D_3$ ($10^{-8}$ M)+ChM-I 10 µg/mL; and E, $1,25(OH)_2D_3$ ($10^{-8}$M)+ChM-I 25 µg/mL).
Figure 13:
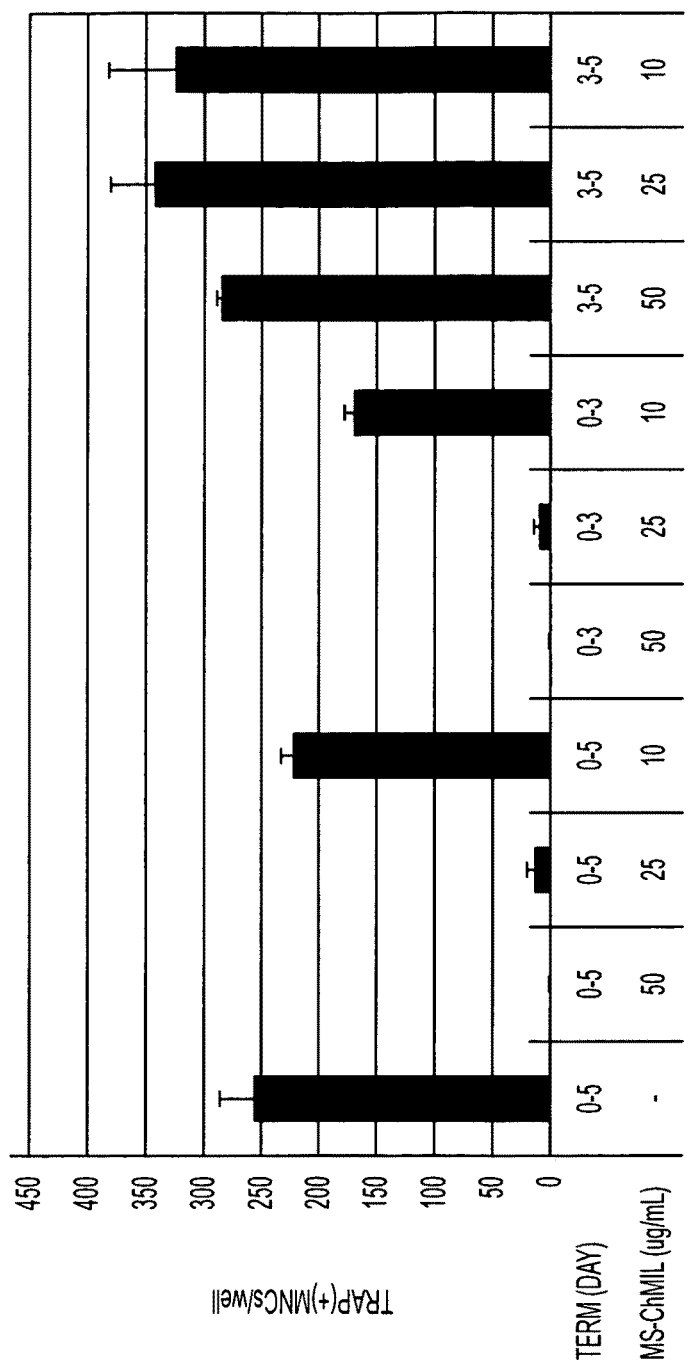
FIG. 13 shows that MS-ChM1L directly acts on differentiation of osteoclast precursor cells in an early stage to inhibit the differentiation, where its inhibitory action is irreversible.
Figure 14:
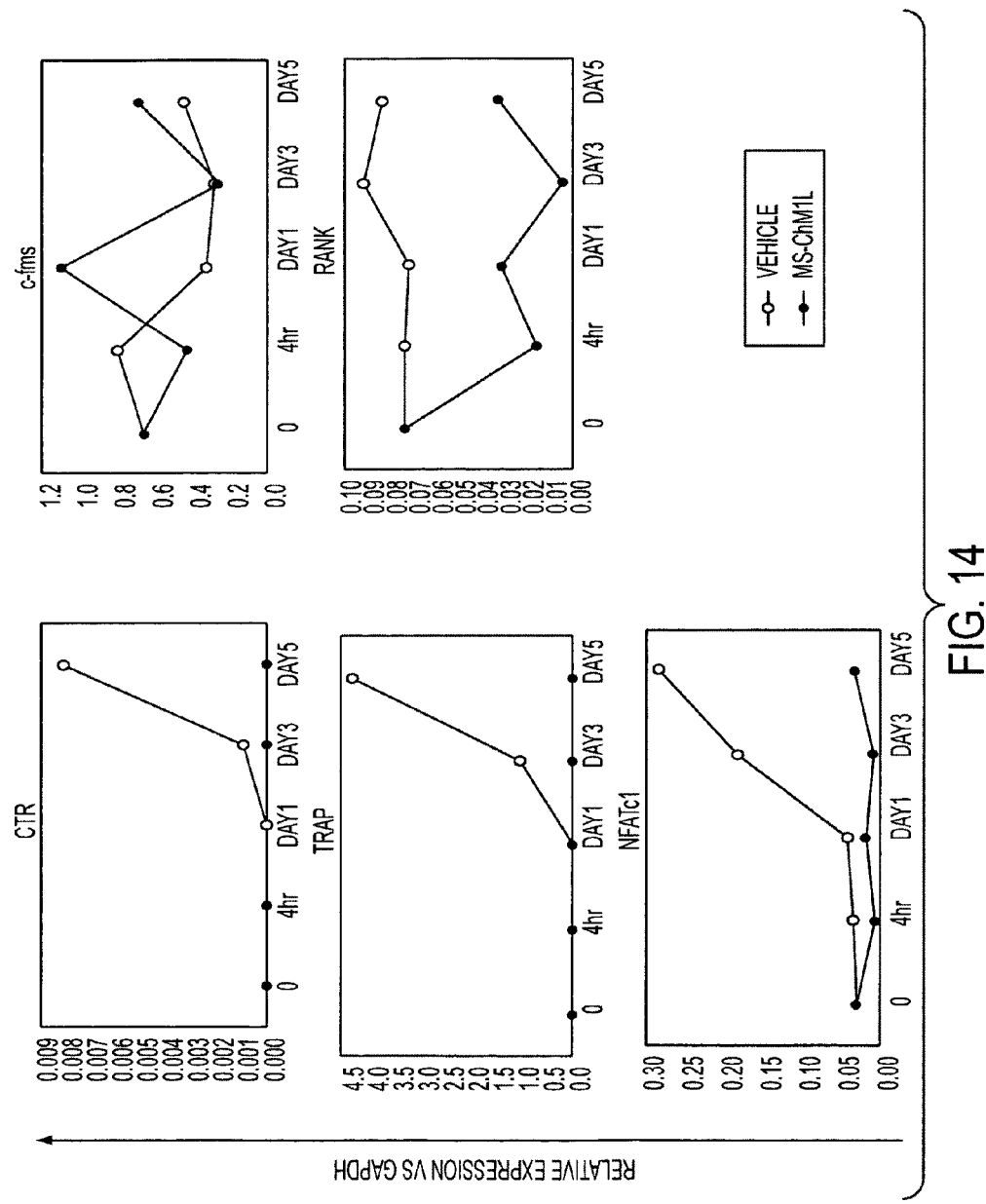
FIG. 14 shows an analysis result of expression of an osteoclast marker gene.
Figure 15:
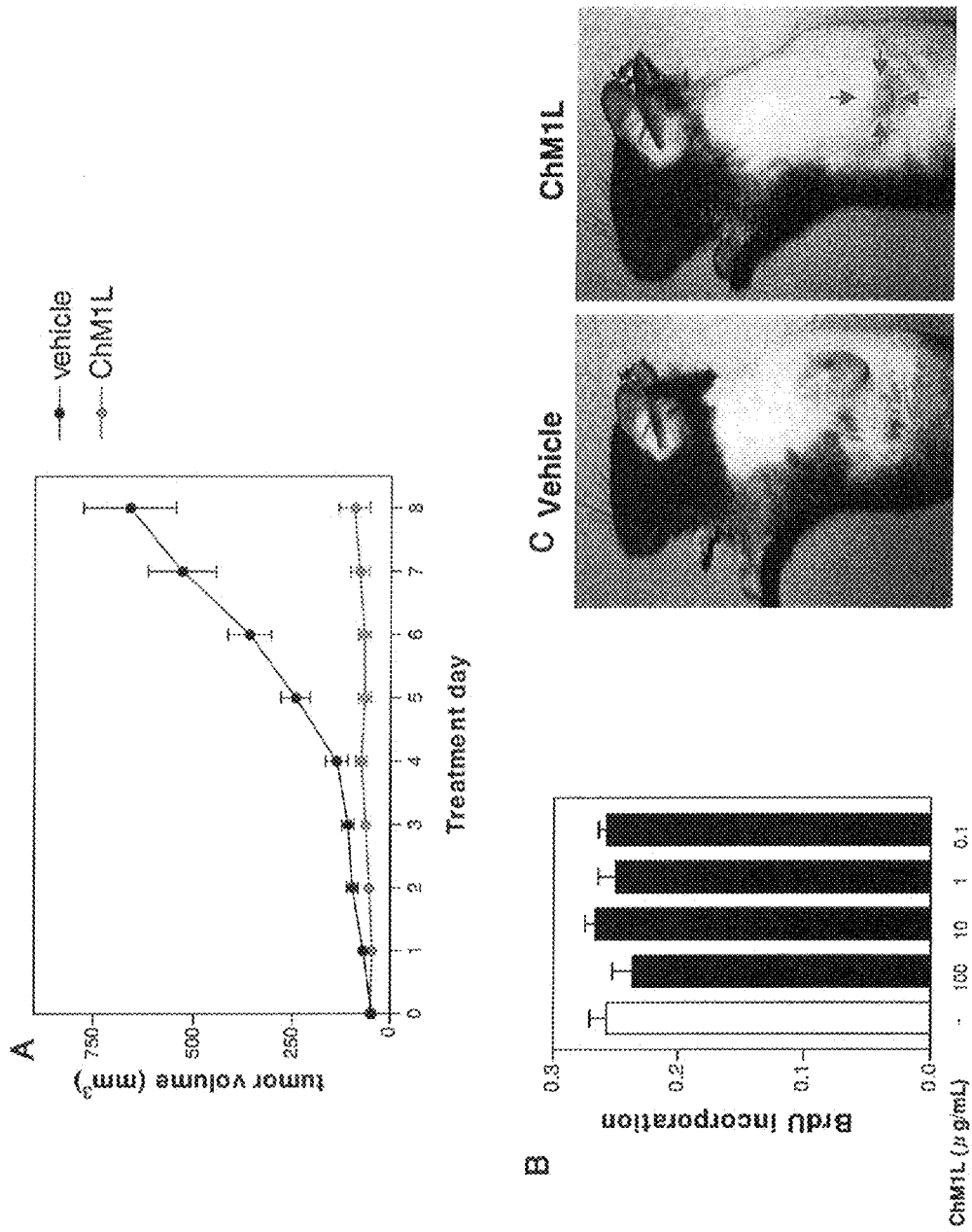
FIG. 15 shows an analysis result of the inhibitory action of administered MS-ChM1L on growth of B16F10 melanoma, wherein the growth of B16F10 melanoma is inhibited in vivo by administration of MS-ChM1L (A, C), whereas MS-ChM1L does not inhibit in vitro growth of B16F10 melanoma cells.
Figure 16:
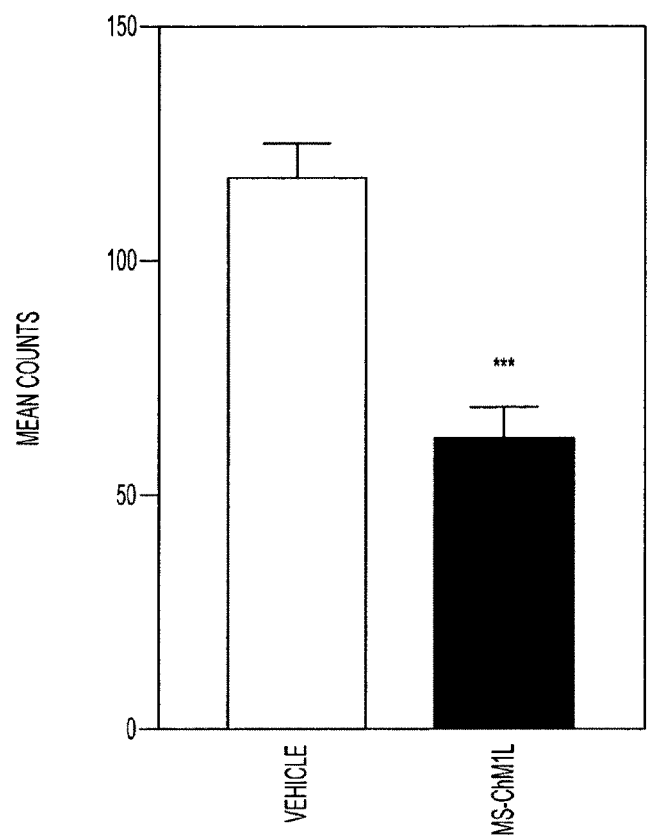
FIG. 16 shows that MS-ChM1L inhibits metastasis of B16F10 melanoma to the lung.
Figure 17:
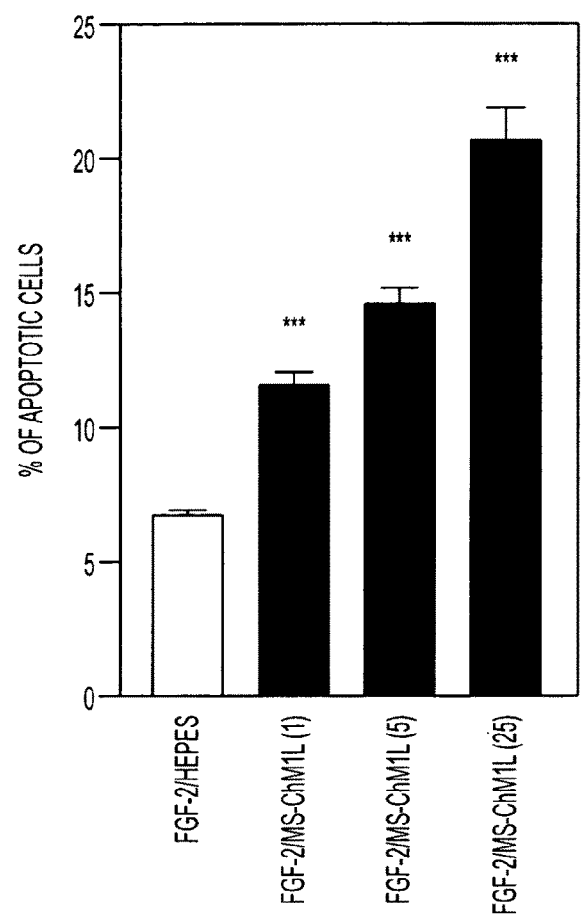
FIG. 17 shows that MS-ChM1L induces apoptosis of vascular endothelial cells.
Figure 18:
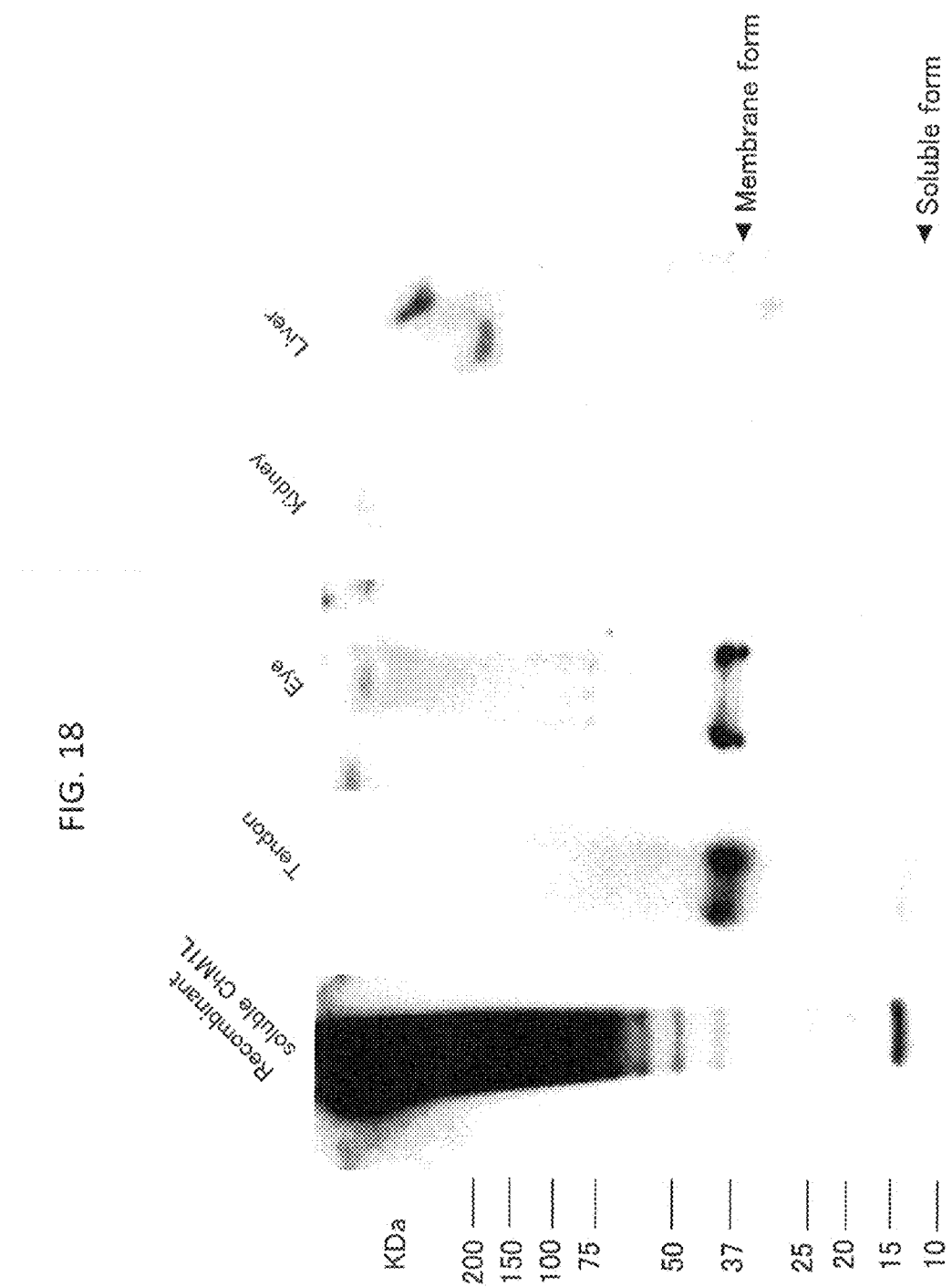
FIG. 18 shows that soluble MS-ChM1L is present in tendon tissue.
Figure 19:
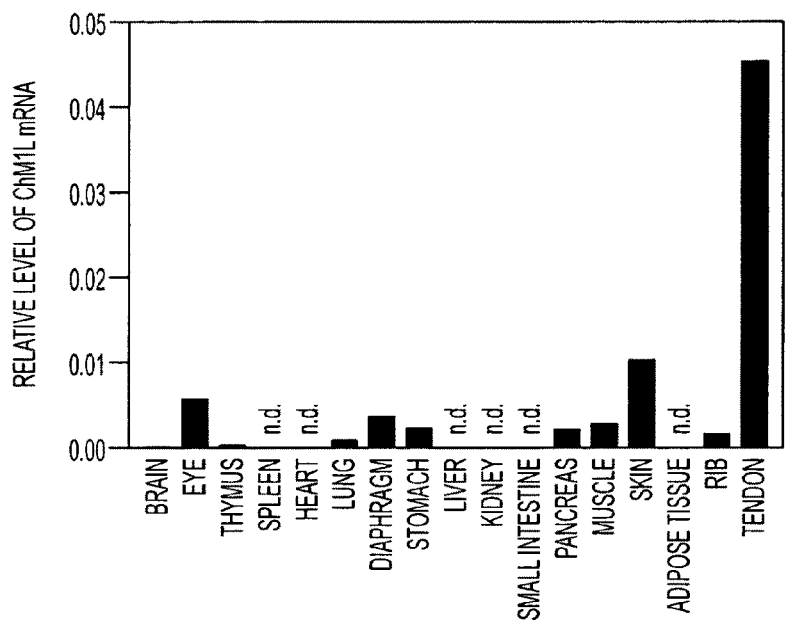
FIG. 19 shows that ChM1L mRNA is expressed specifically in a tendon in living tissues.
Figure 20:
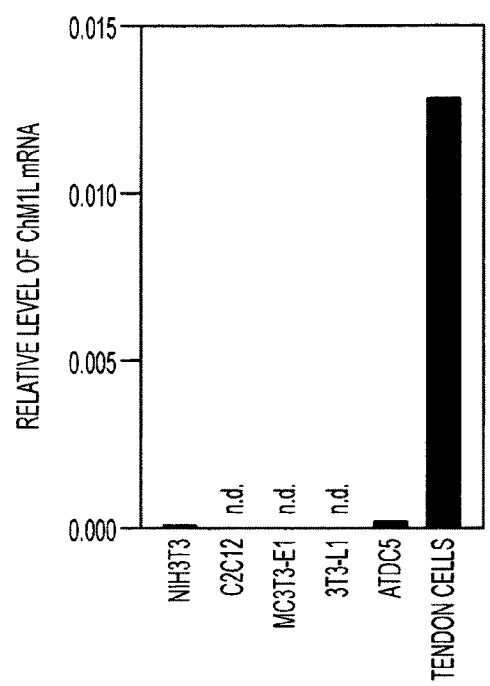
FIG. 20 shows that ChM1L mRNA is expressed specifically in tendon cells among mesenchyme cells.
Figure 21B:
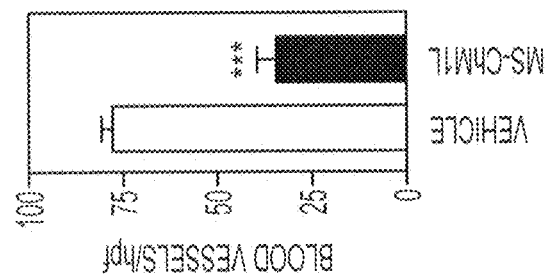
FIG. 21 shows that MS-ChM1L inhibits tumor angiogenesis.
Figure 21A:
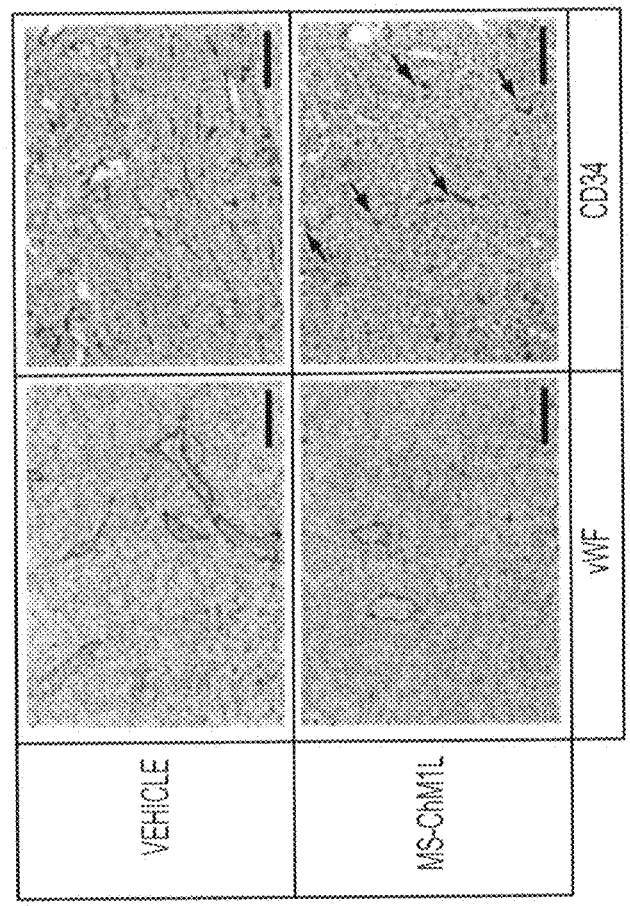
Figure 23:
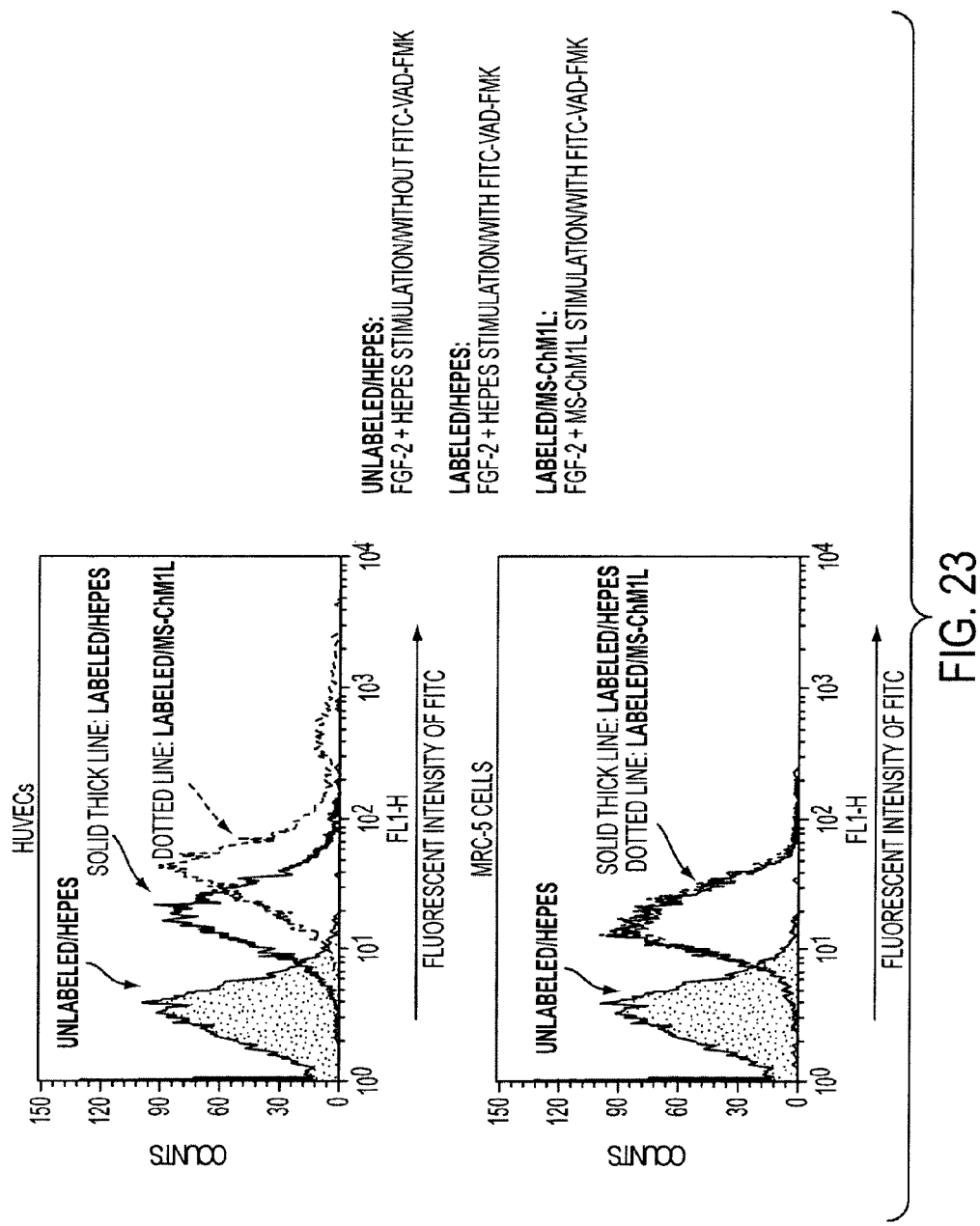
FIG. 23 shows that MS-ChM1L exhibits caspase-mediated apoptosis of vascular endothelial cells.
Figure 24:
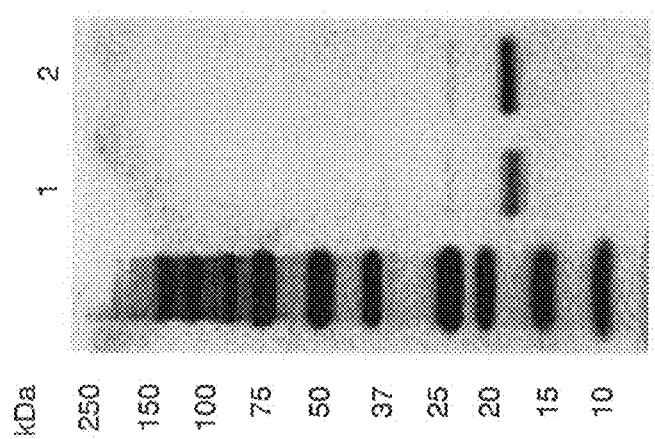
FIG. 24 shows a result of SDS-PAGE, and subsequent staining with GELCODE BLUESTAIN REAGENT™ (Pierce) (protein staining reagents), of purified recombinant ChM-I protein.

```
<160> NUMBER OF SEQ ID NOS: 23

<210> SEQ ID NO 1
<211> LENGTH: 978
<212> TYPE: DNA
<213> ORGANISM: human
<220> FEATURE:
<221> NAME/KEY: CDS
<222> LOCATION: (1)..(951)

<400> SEQUENCE: 1 atg gca aag aat cct cca gag aat tgt gaa gac tgt cac att cta aat        48
Met Ala Lys Asn Pro Pro Glu Asn Cys Glu Asp Cys His Ile Leu Asn
1               5                   10                  15 gca gaa gct ttt aaa tcc aag aaa ata tgt aaa tca ctt aag att tgt        96
Ala Glu Ala Phe Lys Ser Lys Lys Ile Cys Lys Ser Leu Lys Ile Cys
            20                  25                  30 gga ctg gtg ttt ggt atc ctg gcc cta act cta att gtc ctg ttt tgg       144
Gly Leu Val Phe Gly Ile Leu Ala Leu Thr Leu Ile Val Leu Phe Trp
        35                  40                  45 ggg agc aag cac ttc tgg ccg gag gta ccc aaa aaa gcc tat gac atg       192
Gly Ser Lys His Phe Trp Pro Glu Val Pro Lys Lys Ala Tyr Asp Met
    50                  55                  60 gag cac act ttc tac agc aat gga gag aag aag aag att tac atg gaa       240
Glu His Thr Phe Tyr Ser Asn Gly Glu Lys Lys Lys Ile Tyr Met Glu
65                  70                  75                  80 att gat cct gtg acc aga act gaa ata ttc aga agc gga aat ggc act       288
Ile Asp Pro Val Thr Arg Thr Glu Ile Phe Arg Ser Gly Asn Gly Thr
                85                  90                  95 gat gaa aca ttg gaa gta cac gac ttt aaa aac gga tac act ggc atc       336
Asp Glu Thr Leu Glu Val His Asp Phe Lys Asn Gly Tyr Thr Gly Ile
            100                 105                 110 tac ttc gtg ggt ctt caa aaa tgt ttt atc aaa act cag att aaa gtg       384
Tyr Phe Val Gly Leu Gln Lys Cys Phe Ile Lys Thr Gln Ile Lys Val
        115                 120                 125
```

| | | | | | | | | | | | | | | | | |
|---|---|---|---|---|---|---|---|---|---|---|---|---|---|---|---|---|
| att | cct | gaa | ttt | tct | gaa | cca | gaa | gag | gaa | ata | gat | gag | aat | gaa | gaa | 432 |
| Ile | Pro | Glu | Phe | Ser | Glu | Pro | Glu | Glu | Glu | Ile | Asp | Glu | Asn | Glu | Glu | |
| | 130 | | | | 135 | | | | 140 | | | | | | | |
| att | acc | aca | act | ttc | ttt | gaa | cag | tca | gtg | att | tgg | gtc | cca | gca | gaa | 480 |
| Ile | Thr | Thr | Thr | Phe | Phe | Glu | Gln | Ser | Val | Ile | Trp | Val | Pro | Ala | Glu | |
| 145 | | | | | 150 | | | | | 155 | | | | | 160 | |
| aag | cct | att | gaa | aac | cga | gat | ttt | ctt | aaa | aat | tcc | aaa | att | ctg | gag | 528 |
| Lys | Pro | Ile | Glu | Asn | Arg | Asp | Phe | Leu | Lys | Asn | Ser | Lys | Ile | Leu | Glu | |
| | | | 165 | | | | | 170 | | | | | 175 | | | |
| att | tgt | gat | aac | gtg | acc | atg | tat | tgg | atc | aat | ccc | act | cta | ata | tca | 576 |
| Ile | Cys | Asp | Asn | Val | Thr | Met | Tyr | Trp | Ile | Asn | Pro | Thr | Leu | Ile | Ser | |
| | | | 180 | | | | | 185 | | | | | 190 | | | |
| gtt | tct | gag | tta | caa | gac | ttt | gag | gag | gag | gga | gaa | gat | ctt | cac | ttt | 624 |
| Val | Ser | Glu | Leu | Gln | Asp | Phe | Glu | Glu | Glu | Gly | Glu | Asp | Leu | His | Phe | |
| | | 195 | | | | | 200 | | | | | 205 | | | | |
| cct | gcc | aac | gaa | aaa | aaa | ggg | att | gaa | caa | aat | gaa | cag | tgg | gtg | gtc | 672 |
| Pro | Ala | Asn | Glu | Lys | Lys | Gly | Ile | Glu | Gln | Asn | Glu | Gln | Trp | Val | Val | |
| | 210 | | | | 215 | | | | | 220 | | | | | | |
| cct | caa | gtg | aaa | gta | gag | aag | acc | cgt | cac | gcc | aga | caa | gca | agt | gag | 720 |
| Pro | Gln | Val | Lys | Val | Glu | Lys | Thr | Arg | His | Ala | Arg | Gln | Ala | Ser | Glu | |
| 225 | | | | | 230 | | | | 235 | | | | | | 240 | |
| gaa | gaa | ctt | cca | ata | aat | gac | tat | act | gaa | aat | gga | ata | gaa | ttt | gat | 768 |
| Glu | Glu | Leu | Pro | Ile | Asn | Asp | Tyr | Thr | Glu | Asn | Gly | Ile | Glu | Phe | Asp | |
| | | | | 245 | | | | | 250 | | | | | 255 | | |
| ccc | atg | ctg | gat | gag | aga | ggt | tat | tgt | tgt | att | tac | tgc | cgt | cga | ggc | 816 |
| Pro | Met | Leu | Asp | Glu | Arg | Gly | Tyr | Cys | Cys | Ile | Tyr | Cys | Arg | Arg | Gly | |
| | | 260 | | | | | 265 | | | | | 270 | | | | |
| aac | cgc | tat | tgc | cgc | cgc | gtc | tgt | gaa | cct | tta | cta | ggc | tac | tac | cca | 864 |
| Asn | Arg | Tyr | Cys | Arg | Arg | Val | Cys | Glu | Pro | Leu | Leu | Gly | Tyr | Tyr | Pro | |
| | | 275 | | | | | 280 | | | | | 285 | | | | |
| tat | cca | tac | tgc | tac | caa | gga | gga | cga | gtc | atc | tgt | cgt | gtc | atc | atg | 912 |
| Tyr | Pro | Tyr | Cys | Tyr | Gln | Gly | Gly | Arg | Val | Ile | Cys | Arg | Val | Ile | Met | |
| | 290 | | | | | 295 | | | | | 300 | | | | | |
| cct | tgt | aac | tgg | tgg | gtg | gcc | cgc | atg | ctg | ggg | agg | gtc | gactacaaag | | | 961 |
| Pro | Cys | Asn | Trp | Trp | Val | Ala | Arg | Met | Leu | Gly | Arg | Val | | | | |
| 305 | | | | 310 | | | | | 315 | | | | | | | |
| acgatgacga caagtga | | | | | | | | | | | | | | | | 978 |

<210> SEQ ID NO 2
<211> LENGTH: 317
<212> TYPE: PRT
<213> ORGANISM: human

<400> SEQUENCE: 2

Met Ala Lys Asn Pro Pro Glu Asn Cys Glu Asp Cys His Ile Leu Asn
1               5                   10                  15

Ala Glu Ala Phe Lys Ser Lys Lys Ile Cys Lys Ser Leu Lys Ile Cys
                20                  25                  30

Gly Leu Val Phe Gly Ile Leu Ala Leu Thr Leu Ile Val Leu Phe Trp
            35                  40                  45

Gly Ser Lys His Phe Trp Pro Glu Val Pro Lys Lys Ala Tyr Asp Met
        50                  55                  60

Glu His Thr Phe Tyr Ser Asn Gly Glu Lys Lys Lys Ile Tyr Met Glu
65                  70                  75                  80

Ile Asp Pro Val Thr Arg Thr Glu Ile Phe Arg Ser Gly Asn Gly Thr
                85                  90                  95

Asp Glu Thr Leu Glu Val His Asp Phe Lys Asn Gly Tyr Thr Gly Ile
            100                 105                 110

```
Tyr Phe Val Gly Leu Gln Lys Cys Phe Ile Lys Thr Gln Ile Lys Val
            115                 120                 125
Ile Pro Glu Phe Ser Glu Pro Glu Glu Ile Asp Glu Asn Glu Glu
130                 135                 140
Ile Thr Thr Thr Phe Phe Glu Gln Ser Val Ile Trp Val Pro Ala Glu
145                 150                 155                 160
Lys Pro Ile Glu Asn Arg Asp Phe Leu Lys Asn Ser Lys Ile Leu Glu
                165                 170                 175
Ile Cys Asp Asn Val Thr Met Tyr Trp Ile Asn Pro Thr Leu Ile Ser
            180                 185                 190
Val Ser Glu Leu Gln Asp Phe Glu Glu Glu Gly Glu Asp Leu His Phe
        195                 200                 205
Pro Ala Asn Glu Lys Lys Gly Ile Glu Gln Asn Glu Gln Trp Val Val
    210                 215                 220
Pro Gln Val Lys Val Glu Lys Thr Arg His Ala Arg Gln Ala Ser Glu
225                 230                 235                 240
Glu Glu Leu Pro Ile Asn Asp Tyr Thr Glu Asn Gly Ile Glu Phe Asp
                245                 250                 255
Pro Met Leu Asp Glu Arg Gly Tyr Cys Cys Ile Tyr Cys Arg Arg Gly
            260                 265                 270
Asn Arg Tyr Cys Arg Arg Val Cys Glu Pro Leu Leu Gly Tyr Tyr Pro
        275                 280                 285
Tyr Pro Tyr Cys Tyr Gln Gly Gly Arg Val Ile Cys Arg Val Ile Met
    290                 295                 300
Pro Cys Asn Trp Trp Val Ala Arg Met Leu Gly Arg Val
305                 310                 315

<210> SEQ ID NO 3
<211> LENGTH: 246
<212> TYPE: DNA
<213> ORGANISM: human
<220> FEATURE:
<221> NAME/KEY: CDS
<222> LOCATION: (1)..(246)

<400> SEQUENCE: 3 caa gca agt gag gaa gaa ctt cca ata aat gac tat act gaa aat gga      48
Gln Ala Ser Glu Glu Glu Leu Pro Ile Asn Asp Tyr Thr Glu Asn Gly
1               5                   10                  15 ata gaa ttt gat ccc atg ctg gat gag aga ggt tat tgt tgt att tac      96
Ile Glu Phe Asp Pro Met Leu Asp Glu Arg Gly Tyr Cys Cys Ile Tyr
            20                  25                  30 tgc cgt cga ggc aac cgc tat tgc cgc cgc gtc tgt gaa cct tta cta    144
Cys Arg Arg Gly Asn Arg Tyr Cys Arg Arg Val Cys Glu Pro Leu Leu
        35                  40                  45 ggc tac tac cca tat cca tac tgc tac caa gga gga cga gtc atc tgt    192
Gly Tyr Tyr Pro Tyr Pro Tyr Cys Tyr Gln Gly Gly Arg Val Ile Cys
    50                  55                  60 cgt gtc atc atg cct tgt aac tgg tgg gtg gcc cgc atg ctg ggg agg    240
Arg Val Ile Met Pro Cys Asn Trp Trp Val Ala Arg Met Leu Gly Arg
65                  70                  75                  80 gtc taa                                                             246
Val

<210> SEQ ID NO 4
<211> LENGTH: 81
<212> TYPE: PRT
<213> ORGANISM: human
```

-continued

```
<400> SEQUENCE: 4

Gln Ala Ser Glu Glu Leu Pro Ile Asn Asp Tyr Thr Glu Asn Gly
1               5                   10                  15

Ile Glu Phe Asp Pro Met Leu Asp Glu Arg Gly Tyr Cys Cys Ile Tyr
            20                  25                  30

Cys Arg Arg Gly Asn Arg Tyr Cys Arg Arg Val Cys Glu Pro Leu Leu
        35                  40                  45

Gly Tyr Tyr Pro Tyr Pro Tyr Cys Tyr Gln Gly Gly Arg Val Ile Cys
    50                  55                  60

Arg Val Ile Met Pro Cys Asn Trp Trp Val Ala Arg Met Leu Gly Arg
65                  70                  75                  80

Val

<210> SEQ ID NO 5
<211> LENGTH: 303
<212> TYPE: DNA
<213> ORGANISM: human
<220> FEATURE:
<221> NAME/KEY: CDS
<222> LOCATION: (1)..(303)

<400> SEQUENCE: 5 atg cac cat cat cat cat cat gat atc gac tac aaa gac gat gac gac        48
Met His His His His His His Asp Ile Asp Tyr Lys Asp Asp Asp Asp
1               5                   10                  15 aag tcg cga caa gca agt gag gaa gaa ctt cca ata aat gac tat act        96
Lys Ser Arg Gln Ala Ser Glu Glu Glu Leu Pro Ile Asn Asp Tyr Thr
            20                  25                  30 gaa aat gga ata gaa ttt gat ccc atg ctg gat gag aga ggt tat tgt       144
Glu Asn Gly Ile Glu Phe Asp Pro Met Leu Asp Glu Arg Gly Tyr Cys
        35                  40                  45 tgt att tac tgc cgt cga ggc aac cgc tat tgc cgc cgc gtc tgt gaa       192
Cys Ile Tyr Cys Arg Arg Gly Asn Arg Tyr Cys Arg Arg Val Cys Glu
    50                  55                  60 cct tta cta ggc tac tac cca tat cca tac tgc tac caa gga gga cga       240
Pro Leu Leu Gly Tyr Tyr Pro Tyr Pro Tyr Cys Tyr Gln Gly Gly Arg
65              70                  75                  80 gtc atc tgt cgt gtc atc atg cct tgt aac tgg tgg gtg gcc cgc atg       288
Val Ile Cys Arg Val Ile Met Pro Cys Asn Trp Trp Val Ala Arg Met
                85                  90                  95 ctg ggg agg gtc taa                                                    303
Leu Gly Arg Val
            100

<210> SEQ ID NO 6
<211> LENGTH: 100
<212> TYPE: PRT
<213> ORGANISM: human

<400> SEQUENCE: 6

Met His His His His His His Asp Ile Asp Tyr Lys Asp Asp Asp Asp
1               5                   10                  15

Lys Ser Arg Gln Ala Ser Glu Glu Glu Leu Pro Ile Asn Asp Tyr Thr
            20                  25                  30

Glu Asn Gly Ile Glu Phe Asp Pro Met Leu Asp Glu Arg Gly Tyr Cys
        35                  40                  45

Cys Ile Tyr Cys Arg Arg Gly Asn Arg Tyr Cys Arg Arg Val Cys Glu
    50                  55                  60

Pro Leu Leu Gly Tyr Tyr Pro Tyr Pro Tyr Cys Tyr Gln Gly Gly Arg
65              70                  75                  80
```

```
Val Ile Cys Arg Val Ile Met Pro Cys Asn Trp Trp Val Ala Arg Met
                85                  90                  95

Leu Gly Arg Val
        100

<210> SEQ ID NO 7
<211> LENGTH: 420
<212> TYPE: DNA
<213> ORGANISM: human
<220> FEATURE:
<221> NAME/KEY: CDS
<222> LOCATION: (1)..(420)

<400> SEQUENCE: 7 atg cac cat cat cat cat cat gat atc gac tac aaa gac gat gac gac      48
Met His His His His His His Asp Ile Asp Tyr Lys Asp Asp Asp Asp
1               5                   10                  15 aag tcg cga gaa gtg gta aga aaa att gtt cca act acc aca aaa aga      96
Lys Ser Arg Glu Val Val Arg Lys Ile Val Pro Thr Thr Thr Lys Arg
                20                  25                  30 cca cac agt gga cca cgg agc aac cca ggc gct gga aga ctg aat aat     144
Pro His Ser Gly Pro Arg Ser Asn Pro Gly Ala Gly Arg Leu Asn Asn
            35                  40                  45 gaa acc aga ccc agt gtt caa gag gac tca caa gcc ttc aat cct gat     192
Glu Thr Arg Pro Ser Val Gln Glu Asp Ser Gln Ala Phe Asn Pro Asp
        50                  55                  60 aat cct tat cat cag cag gaa ggg gaa agc atg aca ttc gac cct aga     240
Asn Pro Tyr His Gln Gln Glu Gly Glu Ser Met Thr Phe Asp Pro Arg
65                  70                  75                  80 ctg gat cac gaa gga atc tgt tgt ata gaa tgt agg cgg agc tac acc     288
Leu Asp His Glu Gly Ile Cys Cys Ile Glu Cys Arg Arg Ser Tyr Thr
                85                  90                  95 cac tgc cag aag atc tgt gaa ccc ctg ggg ggc tat tac cca tgg cct     336
His Cys Gln Lys Ile Cys Glu Pro Leu Gly Gly Tyr Tyr Pro Trp Pro
                100                 105                 110 tat aat tat caa ggc tgc cgt tcg gcc tgc aga gtc atc atg cca tgt     384
Tyr Asn Tyr Gln Gly Cys Arg Ser Ala Cys Arg Val Ile Met Pro Cys
            115                 120                 125 agc tgg tgg gtg gcc cgt atc ttg ggc atg gtg tga                     420
Ser Trp Trp Val Ala Arg Ile Leu Gly Met Val
        130                 135

<210> SEQ ID NO 8
<211> LENGTH: 139
<212> TYPE: PRT
<213> ORGANISM: human

<400> SEQUENCE: 8

Met His His His His His His Asp Ile Asp Tyr Lys Asp Asp Asp Asp
1               5                   10                  15

Lys Ser Arg Glu Val Val Arg Lys Ile Val Pro Thr Thr Thr Lys Arg
                20                  25                  30

Pro His Ser Gly Pro Arg Ser Asn Pro Gly Ala Gly Arg Leu Asn Asn
            35                  40                  45

Glu Thr Arg Pro Ser Val Gln Glu Asp Ser Gln Ala Phe Asn Pro Asp
        50                  55                  60

Asn Pro Tyr His Gln Gln Glu Gly Glu Ser Met Thr Phe Asp Pro Arg
65                  70                  75                  80

Leu Asp His Glu Gly Ile Cys Cys Ile Glu Cys Arg Arg Ser Tyr Thr
                85                  90                  95
```

His Cys Gln Lys Ile Cys Glu Pro Leu Gly Gly Tyr Tyr Pro Trp Pro
            100                 105                 110

Tyr Asn Tyr Gln Gly Cys Arg Ser Ala Cys Arg Val Ile Met Pro Cys
            115                 120                 125

Ser Trp Trp Val Ala Arg Ile Leu Gly Met Val
            130                 135

<210> SEQ ID NO 9
<211> LENGTH: 80
<212> TYPE: PRT
<213> ORGANISM: human

<400> SEQUENCE: 9

Ala Ser Glu Glu Glu Leu Pro Ile Asn Asp Tyr Thr Glu Asn Gly Ile
1               5                   10                  15

Glu Phe Asp Pro Met Leu Asp Glu Arg Gly Tyr Cys Cys Ile Tyr Cys
            20                  25                  30

Arg Arg Gly Asn Arg Tyr Cys Arg Arg Val Cys Glu Pro Leu Leu Gly
            35                  40                  45

Tyr Tyr Pro Tyr Pro Tyr Cys Tyr Gln Gly Gly Arg Val Ile Cys Arg
    50                  55                  60

Val Ile Met Pro Cys Asn Trp Trp Val Ala Arg Met Leu Gly Arg Val
65                  70                  75                  80

<210> SEQ ID NO 10
<211> LENGTH: 8
<212> TYPE: PRT
<213> ORGANISM: Artificial Sequence
<220> FEATURE:
<223> OTHER INFORMATION: FLAG TAG

<400> SEQUENCE: 10

Asp Tyr Lys Asp Asp Asp Asp Lys
1               5

<210> SEQ ID NO 11
<211> LENGTH: 7
<212> TYPE: PRT
<213> ORGANISM: human

<400> SEQUENCE: 11

Ala Ser Glu Glu Glu Leu Pro
1               5

<210> SEQ ID NO 12
<211> LENGTH: 19
<212> TYPE: DNA
<213> ORGANISM: Artificial Sequence
<220> FEATURE:
<223> OTHER INFORMATION: CTR forward primer

<400> SEQUENCE: 12 gtg ctc ctc ggg ctg tag c                                    19

<210> SEQ ID NO 13
<211> LENGTH: 21
<212> TYPE: DNA
<213> ORGANISM: Artificial Sequence
<220> FEATURE:
<223> OTHER INFORMATION: CTR reverse primer

<400> SEQUENCE: 13 gag gat tcc gtg gtt cct gat                                  21

```
<210> SEQ ID NO 14
<211> LENGTH: 20
<212> TYPE: DNA
<213> ORGANISM: Artificial Sequence
<220> FEATURE:
<223> OTHER INFORMATION: TRAP forward primer

<400> SEQUENCE: 14 gat ccc tct gtg cga cat ca                                          20

<210> SEQ ID NO 15
<211> LENGTH: 20
<212> TYPE: DNA
<213> ORGANISM: Artificial Sequence
<220> FEATURE:
<223> OTHER INFORMATION: TRAP reverse primer

<400> SEQUENCE: 15 cca ggg agt cct cag atc ca                                          20

<210> SEQ ID NO 16
<211> LENGTH: 21
<212> TYPE: DNA
<213> ORGANISM: Artificial Sequence
<220> FEATURE:
<223> OTHER INFORMATION: c-fms forward primer

<400> SEQUENCE: 16 tgg cat ctg gct taa ggt gaa                                         21

<210> SEQ ID NO 17
<211> LENGTH: 20
<212> TYPE: DNA
<213> ORGANISM: Artificial Sequence
<220> FEATURE:
<223> OTHER INFORMATION: c-fms reverse primer

<400> SEQUENCE: 17 gaa tcc gca cca gct tgc ta                                          20

<210> SEQ ID NO 18
<211> LENGTH: 19
<212> TYPE: DNA
<213> ORGANISM: Artificial Sequence
<220> FEATURE:
<223> OTHER INFORMATION: RANK forward primer

<400> SEQUENCE: 18 atg agt aca cgg acc ggc c                                           19

<210> SEQ ID NO 19
<211> LENGTH: 22
<212> TYPE: DNA
<213> ORGANISM: Artificial Sequence
<220> FEATURE:
<223> OTHER INFORMATION: RANK reverse primer

<400> SEQUENCE: 19 gct gga tta gga gca gtg aac c                                       22

<210> SEQ ID NO 20
<211> LENGTH: 20
<212> TYPE: DNA
<213> ORGANISM: Artificial Sequence
<220> FEATURE:
<223> OTHER INFORMATION: NFATc1 forward primer
```

```
<400> SEQUENCE: 20 agg ctg gtc ttc cga gtt ca                                          20

<210> SEQ ID NO 21
<211> LENGTH: 19
<212> TYPE: DNA
<213> ORGANISM: Artificial Sequence
<220> FEATURE:
<223> OTHER INFORMATION: NFATc1 reverse primer

<400> SEQUENCE: 21 acc gct ggg aac act cga t                                           19

<210> SEQ ID NO 22
<211> LENGTH: 22
<212> TYPE: DNA
<213> ORGANISM: Artificial Sequence
<220> FEATURE:
<223> OTHER INFORMATION: Mouse ChM1L forward primer

<400> SEQUENCE: 22 aaa cac ttc tgg ccc gag gta t                                       22

<210> SEQ ID NO 23
<211> LENGTH: 25
<212> TYPE: DNA
<213> ORGANISM: Artificial Sequence
<220> FEATURE:
<223> OTHER INFORMATION: Mouse ChM1L reverse primer

<400> SEQUENCE: 23 agt gtg ctc cat gtc ata ggt ttt c                                   25
```

The invention claimed is:

1. A soluble polypeptide having an activity of inhibiting angiogenesis and/or an activity of inhibiting bone resorption selected from the group consisting of:
   (a) a polypeptide consisting of the amino acid sequence of SEQ ID NO: 9;
   (b) a polypeptide of (a), which further has a tag sequence added to the N-terminal or C-terminal thereof consisting of about 6 to about 8 consecutive histidine residues;
   (c) a polypeptide of (a), which further has a FLAG tag sequence added to the N-terminal or C-terminal thereof;
   (d) a polypeptide of (a), which further has tag sequences added to the N-terminal and/or C-terminal thereof consisting of about 6 to about 8 consecutive histidine residues and a FLAG tag sequence;
   (e) a polypeptide of (a) to (d), which further has a methionine residue at the N-terminal thereof;
   (f) a polypeptide of (a), which further has a glutamine residue at the N-terminal thereof;
   (g) a polypeptide of (a), which further has a pyro-glutamine residue at the N-terminal thereof;
   (h) a polypeptide of (b) to (d), wherein the amino acid residues added to the N-terminal and/or C-terminal thereof contain modified amino acid residues, which have at least one modified group selected from the group consisting of an acetyl group, formyl group, biotin group, Boc group and Fmoc group.

2. A composition comprising polypeptide of claim 1.

* * * * *